United States Patent
Patil et al.

(10) Patent No.: US 12,133,764 B2
(45) Date of Patent: Nov. 5, 2024

(54) SYSTEMS AND METHODS FOR AN ADAPTIVE INTERFACE FOR AN ULTRASOUND IMAGING SYSTEM

(71) Applicant: GE Precision Healthcare LLC, Milwaukee, WI (US)

(72) Inventors: Mahendra Madhukar Patil, Bangalore (IN); Ashish Handa, Bangalore (IN); Raveesh Reddy Sreenivasaiah, Bangalore (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 401 days.

(21) Appl. No.: 17/148,376

(22) Filed: Jan. 13, 2021

(65) Prior Publication Data

US 2022/0087644 A1    Mar. 24, 2022

(30) Foreign Application Priority Data

Sep. 24, 2020 (IN) .............................. 202041041436

(51) Int. Cl.
 *A61B 8/00* (2006.01)
 *A61B 8/08* (2006.01)
 (Continued)

(52) U.S. Cl.
 CPC .................. *A61B 8/42* (2013.01); *A61B 8/46* (2013.01); *A61B 8/463* (2013.01); *A61B 8/5215* (2013.01);
 (Continued)

(58) Field of Classification Search
 USPC ............................................................ 705/2
 See application file for complete search history.

(56) References Cited

U.S. PATENT DOCUMENTS

| 8,831,314 B1 | 9/2014 | Fonte et al. |
| 10,628,001 B2 | 4/2020 | Adam et al. |

(Continued)

FOREIGN PATENT DOCUMENTS

| CN | 105138250 A | 12/2015 |
| CN | 111053573 A | 4/2020 |

OTHER PUBLICATIONS

Kramers, M. K. (2014). Evaluating human performance for image-guided surgical tasks (Order No. 29242526). Available from ProQuest Dissertations and Theses Professional. (2701128441). Retrieved from https://dialog.proquest.com/professional/docview/2701128441?accountid=131444 (Year: 2014).*

(Continued)

*Primary Examiner* — Robert W Morgan
*Assistant Examiner* — Bennett Stephen Erickson
(74) *Attorney, Agent, or Firm* — McCoy Russell LLP

(57) ABSTRACT

Various methods and systems are provided for dynamically adjusting user guidance based on a user's proficiency by tracking the same. In one example, a proficiency score for a user may be tracked over time and practice based on a pre-defined rubric for a given anatomical region and a given anatomical target within the anatomical region. During medical imaging, based on the proficiency score of the user, an amount of user guidance that is provided to the user may be adjusted. For example, user guidance may be automatically activated to guide the user during the imaging procedure when the proficiency score of the user is less than a threshold score.

22 Claims, 13 Drawing Sheets

(51) Int. Cl.
   *G09B 19/00* (2006.01)
   *G16H 40/63* (2018.01)
(52) U.S. Cl.
   CPC ............ *G16H 40/63* (2018.01); *A61B 8/4427* (2013.01); *A61B 8/4472* (2013.01); *A61B 8/461* (2013.01); *A61B 8/5292* (2013.01); *G09B 19/003* (2013.01)

(56) References Cited

U.S. PATENT DOCUMENTS

| | | | | |
|---|---|---|---|---|
| 10,885,151 | B2* | 1/2021 | Fung | G16H 20/40 |
| 2005/0119568 | A1* | 6/2005 | Salcudean | G01S 15/8977 |
| | | | | 600/437 |
| 2017/0360401 | A1 | 12/2017 | Rothberg et al. | |
| 2017/0360402 | A1 | 12/2017 | de Jonge et al. | |
| 2018/0365025 | A1 | 12/2018 | Almecija et al. | |
| 2019/0206562 | A1* | 7/2019 | Shelton, IV | A61M 1/79 |
| 2020/0113542 | A1 | 4/2020 | Perrey | |
| 2020/0160511 | A1* | 5/2020 | Lyman | G06F 18/41 |
| 2020/0372714 | A1* | 11/2020 | Soryal | A61B 90/36 |
| 2020/0397511 | A1* | 12/2020 | Ishrak | A61F 2/2427 |
| 2020/0402651 | A1* | 12/2020 | Nesterenko | G16H 50/20 |
| 2021/0082567 | A1* | 3/2021 | Lee | G06F 3/038 |
| 2023/0181148 | A1* | 6/2023 | Mert | A61B 8/0841 |
| | | | | 600/407 |
| 2023/0210491 | A1* | 7/2023 | Joshi | A61B 5/1072 |
| | | | | 600/454 |

OTHER PUBLICATIONS

"Augmented Reality Acquisition software with the Butterfly iQ," YouTube Website, Available Online at https://www.youtube.com/watch?v=dIIOTFyKMVU, Oct. 28, 2017, 4 pages.
Zeldovich, L., "Handheld Ultrasound Devices are Speeding Diagnosis of COVID-19," Scientific American Website, Available Online at https://www.scientificamerican.com/article/handheld-ultrasound-devices-are-speeding-diagnosis-of-covid-19/, Jun. 11, 2020, 8 pages.
Sultan, L. et al., "A Review of Early Experience in Lung Ultrasound in the Diagnosis and Management of COVID-19," Ultrasound in Medicine and Biology, vol. 46, No. 9, Sep. 2020, 17 pages.
Pivetta, E. et al., "Self-Performed Lung Ultrasound for Home Monitoring of a Patient Positive for Coronavirus Disease 2019," CHEST Journal, vol. 158, No. 3, Sep. 1, 2020, 5 pages.
Aminlari, A. et al., "A Case of COVID-19 Diagnosed at Home With Portable Ultrasounds and Confirmed With Home Serology Test," The Journal of Emergency Medicine, vol. 60, No. 3, Oct. 12, 2020, 3 pages.
CN application 202111125620.4 filed Sep. 24, 2021—Office Action issued Aug. 22, 2023; 14 pages.
CN105138250 English Abstract; Espacenet search Nov. 22, 2023; 1 page.

* cited by examiner

| Proficiency parameter | Weight | Anatomical region/ Anatomical target | | | | | Proficiency score |
|---|---|---|---|---|---|---|---|
| | | Level 1 | Level 2 | Level 3 | Level 4 | Level 5 | User Score |
| Image quality | | Qualitative/ quantitative criteria | Qualitative/ quantitative criteria | Qualitative/ quantitative criteria | Qualitative/ quantitative criteria | Qualitative/ quantitative criteria | |
| Acquisition speed | | Quantitative criteria | Quantitative criteria | Quantitative criteria | Quantitative criteria | Quantitative criteria | |
| Scan plane accuracy | | Qualitative/ quantitative criteria | Qualitative/ quantitative criteria | Qualitative/ quantitative criteria | Qualitative/ quantitative criteria | Qualitative/ quantitative criteria | |
| No. practice hours | | Quantitative criteria | Quantitative criteria | Quantitative criteria | Quantitative criteria | Quantitative criteria | |
| No. of exams | | Quantitative criteria | Quantitative criteria | Quantitative criteria | Quantitative criteria | Quantitative criteria | |
| Reproducibility | | Qualitative/ quantitative criteria | Qualitative/ quantitative criteria | Qualitative/ quantitative criteria | Qualitative/ quantitative criteria | Qualitative/ quantitative criteria | |
| Repeatability | | Qualitative/ quantitative criteria | Qualitative/ quantitative criteria | Qualitative/ quantitative criteria | Qualitative/ quantitative criteria | Qualitative/ quantitative criteria | |

FIG. 2A

Abdomen / Liver

| Proficiency parameter | Weight | Level 1 | Level 2 | Level 3 | Level 4 | Level 5 | Proficiency score User Score |
|---|---|---|---|---|---|---|---|
| Image quality | 1.0 | Structure was visualized | Within quality threshold 2 | Within quality threshold 3 | Within quality threshold 4 | Structure + total organ visualized in < 1 minute | |
| Acquisition speed | 0.9 | Within 3 minutes | Within 2.5 minutes | Within 2 minutes | Within 1.5 minutes | Within 1 minute | |
| Scan plane accuracy | 0.7 | Can identify target scan plane | Can identify target scan plane and adjust probe accordingly | Within accuracy threshold 3 | Within accuracy threshold 4 | Within accuracy threshold 5 | |
| No. practice hours | 0.5 | > 4 | > 6 | > 15 | > 25 | > 40 | |
| No. of exams | 0.6 | > 5 | > 10 | > 30 | > 50 | > 100 | |
| Reproducibility | 0.3 | Achieves target scan plane reproducibly across subjects within 60 secs. | Achieves target scan plane reproducibly across subjects within 40 secs. | Achieves target scan plane reproducibly across subjects within 30 secs. | Achieves target scan plane reproducibly across subjects within 20 secs. | Achieves target scan plane reproducibly across subjects within 10 secs. | |
| Repeatability | 0.3 | Achieves target scan plane repeatedly with same subject/conditions within 60 secs. | Achieves target scan plane repeatedly with same subject/conditions within 40 secs. | Achieves target scan plane repeatedly with same subject/conditions within 30 secs. | Achieves target scan plane repeatedly with same subject/conditions within 20 secs. | Achieves target scan plane repeatedly with same subject/conditions within 10 secs. | |

FIG. 2B

Abdomen / Liver

| Proficiency parameter | Weight | Level 1 | Level 2 | Level 3 | Level 4 | Level 5 | User Score |
|---|---|---|---|---|---|---|---|
| | | | | | | | 10.8 |
| Image quality | 1.0 | 1.0 | 1.0 | 1.0 | 0.0 | 0.0 | 3.0 |
| Acquisition speed | 0.9 | 1.0 | 1.0 | 0.0 | 0.0 | 0.0 | 1.8 |
| Scan plane accuracy | 0.7 | 1.0 | 1.0 | 1.0 | 0.0 | 0.0 | 2.1 |
| No. practice hours | 0.5 | 1.0 | 1.0 | 0.0 | 0.0 | 0.0 | 1.0 |
| No. of exams | 0.5 | 1.0 | 1.0 | 0.0 | 0.0 | 0.0 | 1.0 |
| Reproducibility | 0.3 | 1.0 | 1.0 | 1.0 | 0.0 | 0.0 | 1.0 |
| Repeatability | 0.3 | 1.0 | 1.0 | 0.0 | 0.0 | 0.0 | 0.9 |

FIG. 2C

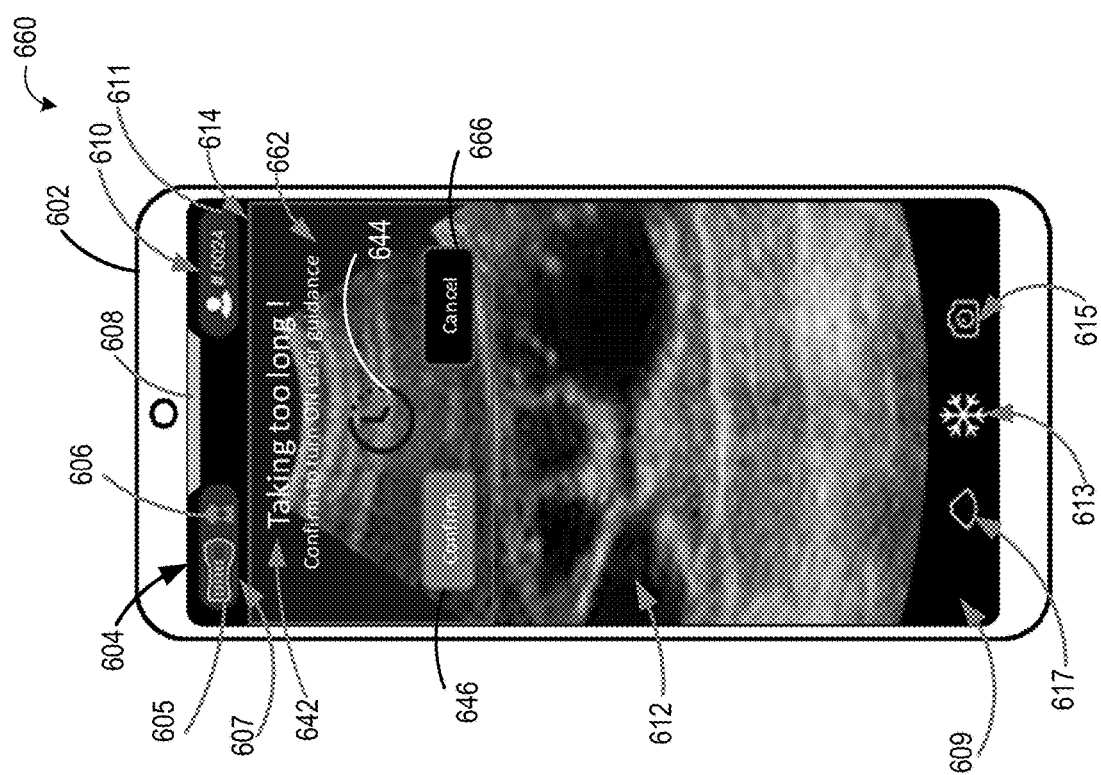
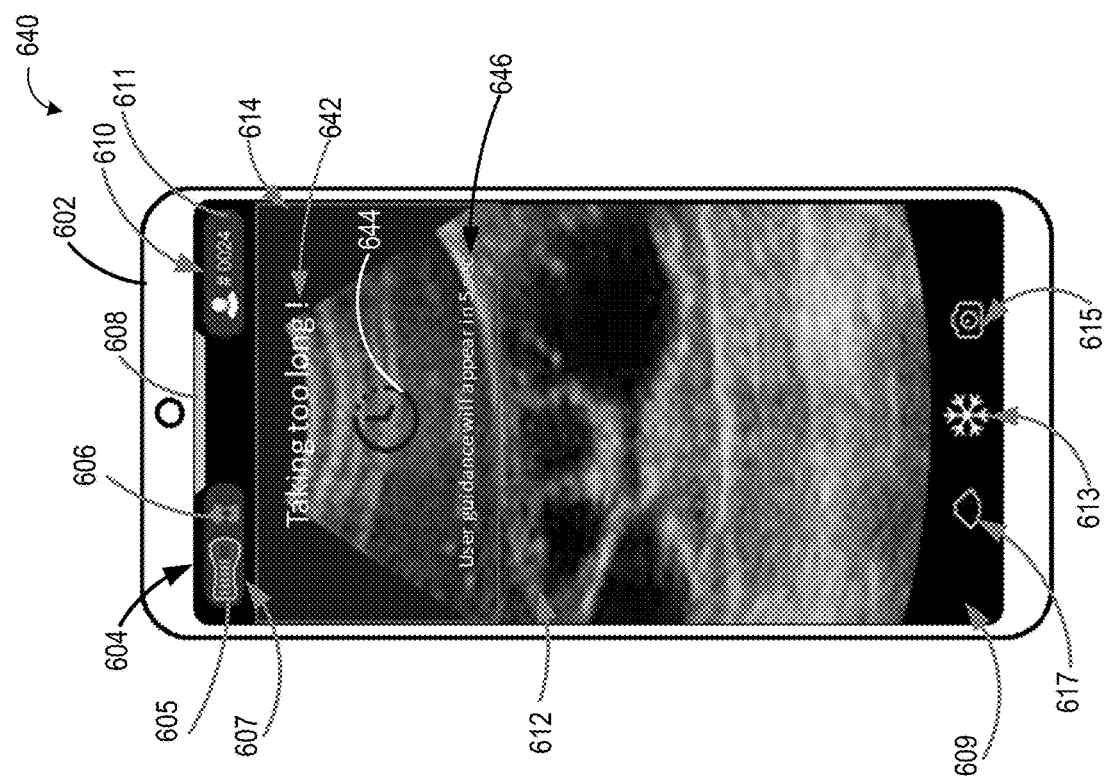
FIG. 6D
FIG. 6C

SYSTEMS AND METHODS FOR AN ADAPTIVE INTERFACE FOR AN ULTRASOUND IMAGING SYSTEM

CROSS-REFERENCE TO RELATED APPLICATIONS

The present application claims priority to Indian Patent Application No. 202041041436, filed on Sep. 24, 2020. The entire contents of the above-listed application is hereby incorporated by reference for all purposes.

TECHNICAL FIELD

Embodiments of the subject matter disclosed herein relate to ultrasound imaging, and more particularly, to user interfaces of ultrasound imaging systems.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image.

Adjusting the placement of the probe to acquire suitable images (e.g., of desired quality) may be difficult. Acquiring suitable images involves adjustment of a location and orientation of the probe on a patient's body, pressure applied to the probe, and adjustment of one or more acquisition parameters (e.g., scan settings) such as transmit frequency, transmit depth, time gain compensation, etc. The process of adjusting the probe may be complicated by variation in patient body types, anatomical features, pathologies, or other factors. As a result, acquiring suitable images involves considerable operator experience, developed as result of a time-consuming trial and error process.

The intense usability requirements and skillful hand-eye co-ordination involved in performing an ultrasound examination make it hard for health care professionals to learn and practice this imaging technique. Example approaches to aid users involve providing real-time scan guidance. However, those solutions do not take into account evolution in skill level, in that the output of the real-time guidance systems in the art is the same for novice users and expert users.

SUMMARY

The current disclosure at least partially addresses one or more of the above identified issues by a method comprising: determining a proficiency score of a user, the proficiency score corresponding to a proficiency of the user in imaging with a medical imaging modality; based on the proficiency score, adjusting an amount of a guidance provided to the user on a graphical user interface of a display device coupled to the medical imaging modality; and displaying an indication of the proficiency on the graphical user interface.

In this way, guidance provided to a user may be customized based on their proficiency in acquiring medical images. Further, as the proficiency of the user evolves with time and practice, the proficiency score may change and thus, the guidance may be adjusted taking into account the evolving proficiency of the user. As a result, user guidance may be automatically adapted to the proficiency of the user, which improves user experience and efficiency.

The above advantages and other advantages, and features of the present description will be readily apparent from the Detailed Description below when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIGS. 2A, 2B, and 2C are exemplary embodiments of a chart for assessing the proficiency of a user of an ultrasound imaging system;

FIGS. 6A, 6B, 6C, and 6D are exemplary embodiments of a user interface for an ultrasound device;

DETAILED DESCRIPTION

Figure 1:
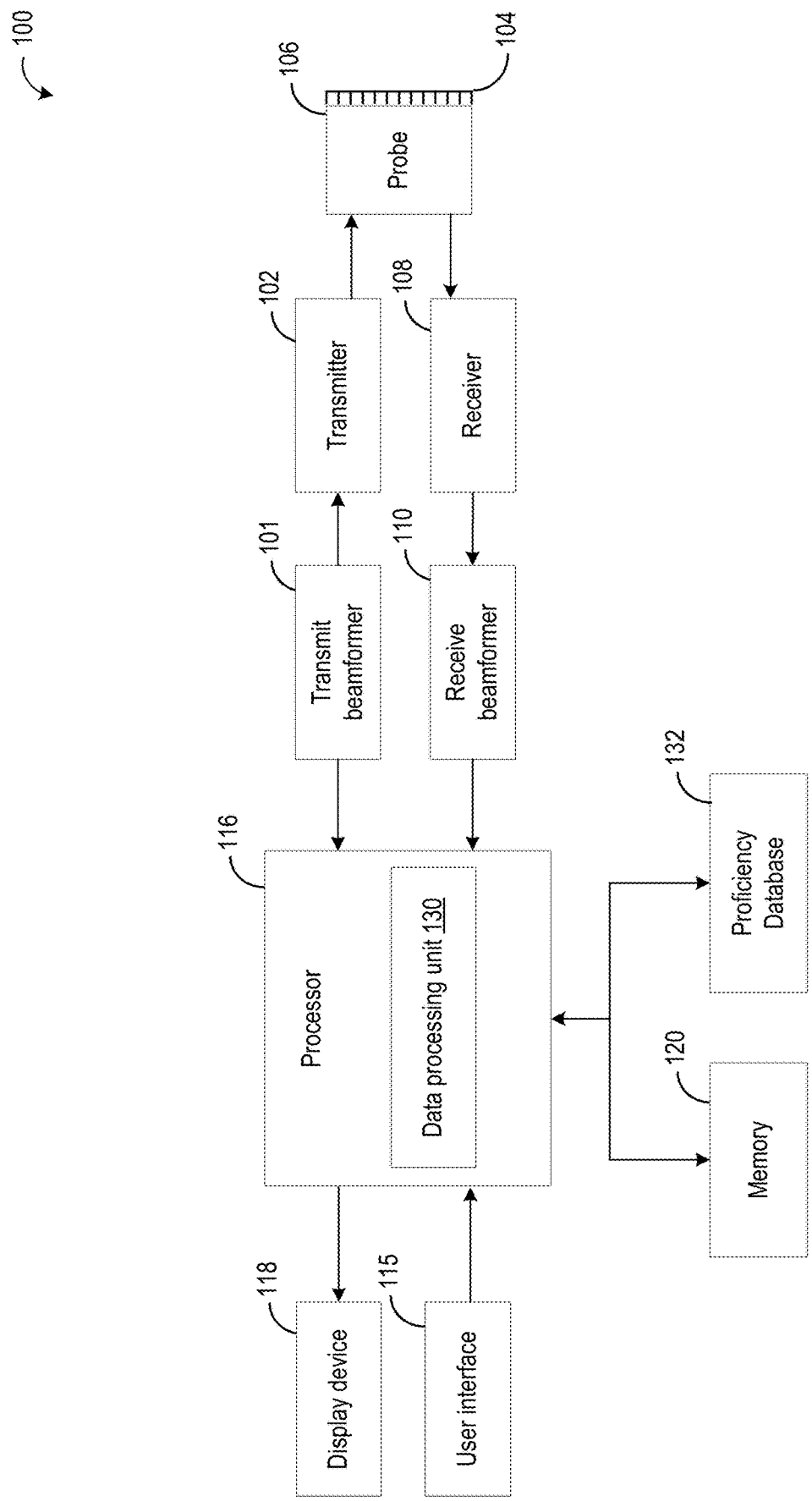
FIG. 1 shows a block diagram of an exemplary embodiment of an ultrasound system.

The following description relates to methods and systems for adjusting user guidance during medical imaging with an imaging modality, such as an ultrasound imaging system, based on tracking a proficiency score of a user. The description herein is provided with respect to an ultrasound imaging system, although it should be appreciated the methods and systems may be adapted to any medical imaging modality, such as mammography, x-ray, computed tomography, MRI, etc., without departing from the scope of the disclosure.

Medical ultrasound imaging typically includes the placement of an ultrasound probe of an ultrasound imaging system, including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of the target anatomical feature (e.g., the heart, the liver, the kidney, etc.). The acquisition parameters that may be adjusted include transmit frequency, transmit depth, gain (e.g., time gain compensation), beam steering angle, beamforming strategy, and/or other parameters. However, varying acquisition parameters and probe placement to acquire an optimal image (e.g., of desired quality) can be challenging, and operator experience is a primary factor in optimal image acquisition.

Further, gaining experience in ultrasound image acquisition is a time consuming, trial-and-error process involving sustained learning and practicing on the part of an ultrasound operator. The process of adjusting the placement of the ultrasound probe until an image is acquired that appears optimal to the operator may not be defined or repeatable/reproducible between exams, and experience gained on one anatomical feature may not transfer well to a different anatomical feature. For example, the experience of an obstetrician in acquiring images of fetuses in pregnant women may not transfer to acquiring images of abnormalities in a spleen of an older man. Thus, an operator who has gained expertise in one anatomical region may not be proficient in another anatomical region. This subjectivity and lack of a defined process may lead to irreproducible results and, in many ultrasound exams, images that are as high quality as possible may not be acquired. Further, during the process of gaining experience, a primary source of aid and support may be in the form of personalized instruction, which is costly and involves a logistical burden of scheduling.

Additionally, proficiency is a factor in the duration of an ultrasound examination. An operator whose proficiency level is low may take longer to acquire suitable images (e.g., images above a desired quality) than an expert operator, which may result in poor patient satisfaction and/or an inability to produce suitable images within the allotted time period. Further, any loss in image quality due to the user's lack of proficiency may result in a poor diagnosis and/or poor clinical outcomes.

One approach to addressing this issue is to provide user guidance, such as a graphical user guidance, to users during ultrasound examinations. For example, user guidance may be displayed in conjunction with or superimposed upon images acquired in real time by the ultrasound probe.

However, the inventors herein have recognized that enabling or disabling the graphical user guidance without taking into account the operator's proficiency level may lead to a poor user experience by the operator, and may not improve the operator's proficiency or help in improving a quality of images acquired. As an example, on-screen graphical user guidance that is helpful to novice users may be a distraction to expert users, while the type of guidance useful to an advanced user may be confusing to a novice user. For example, novice operators may seek proficiency improvement through basic skill development, while expert operators may seek proficiency improvement through increased productivity (e.g., reduced time spent in an examination), or other similar factors. In an embodiment, this problem may be addressed by an adaptive feature that dynamically takes into account an operator's proficiency at the time of the examination, and accordingly enables, disables, and/or selects the type of user guidance most appropriate for the operator.

In this way, the display of guidance to a user may be customized during an examination based on a proficiency of the user, whereby a first type of guidance may be displayed to a novice user, a second type of guidance may be displayed to a more experienced user, a third type of guidance may be displayed to an expert user, and so forth. For example, a novice user performing an examination of a liver of a subject with an ultrasound probe may be shown a reference image of a liver superimposed on an image acquired by the probe during the examination, or a visual indication (e.g., via arrows) of how to perform an adjustment of the probe to visualize a cross-section of the liver. Alternatively, a more experienced user performing an examination of a liver of a subject with an ultrasound probe may be shown an outline of a nodule on the liver that may be hard to see due to being partially obscured by bowel gasses.

In an embodiment, the proficiency of the user may be indicated by a proficiency score displayed on a screen of the ultrasound imaging system. One or more algorithms running on a processor of an ultrasound imaging system, based on instructions stored in a transitory memory of the ultrasound imaging system, may determine how the proficiency score of the user may be determined or adjusted, and/or what type of guidance to display to the user.

Further, a plurality of proficiency scores may be stored in a database accessible by the ultrasound imaging system, each proficiency score of the plurality of proficiency scores reflecting a proficiency of the user on a specific target anatomical feature (e.g., an organ). In this way, guidance displayed to the user may be further customized according to a type of examination being performed, whereby a first type of guidance may be displayed to the user in an examination of an organ on which the user has little experience, and a second type of guidance may be displayed to the user in an examination of a different organ on which the user has more experience. Further, one or more proficiency scores may be used to determine whether to increase an amount of user guidance, or to decrease an amount of user guidance, or to determine what type of user guidance to display to the user.

The proficiency score may be determined and/or updated based on a performance of the user in accordance with a plurality of proficiency parameters, such as a quality of an acquired image, an accuracy of a scan plane, a speed of image acquisition, a reproducibility and/or repeatability of image acquisition, etc. The proficiency parameters may also include historical data, such as a number of examinations performed or hours of practice completed.

An additional advantage of the systems and methods disclosed herein is that the guidance displayed to the user may also be initiated, stopped, increased, or decreased during an examination based on a performance of the user during the examination. For example, if a time taken by the user to acquire an image exceeds a threshold duration, the user may be prompted whether or not to display the guidance, or the guidance may be displayed automatically with or without notification to the user. Additionally, the initiating, stopping, increasing, or decreasing of the guidance may be carried out based on a monitoring of one or more of the proficiency parameters during an examination. For example, a speed of the user in acquiring an image may be monitored, and a type of guidance may be displayed responsive to a speed less than a threshold speed. Further, the initiating, stopping, increasing, or decreasing of different types of guidance may be coordinated and/or displayed in an order or a sequence in accordance with a task or educational goal, such as being incorporated into a training program whereby novice ultrasound users are guided through a procedure, or whereby a performance on a task may be instructed in a standardized manner.

Figure 3A:
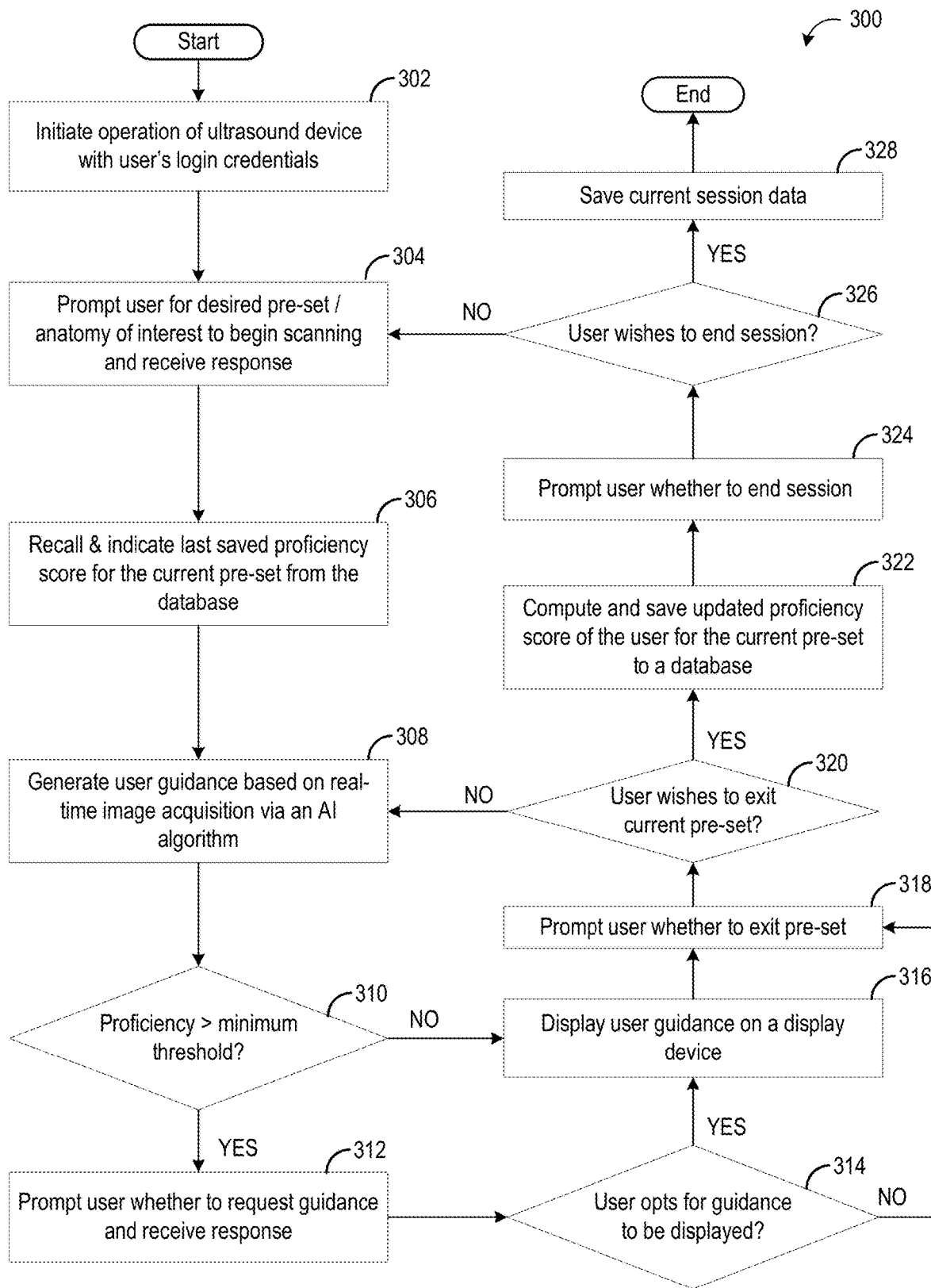
FIGS. 3A, 3B, and 3C are flowcharts illustrating example methods for displaying guidance to a user of an ultrasound imaging system based on a proficiency score of the user.
Figure 6B:
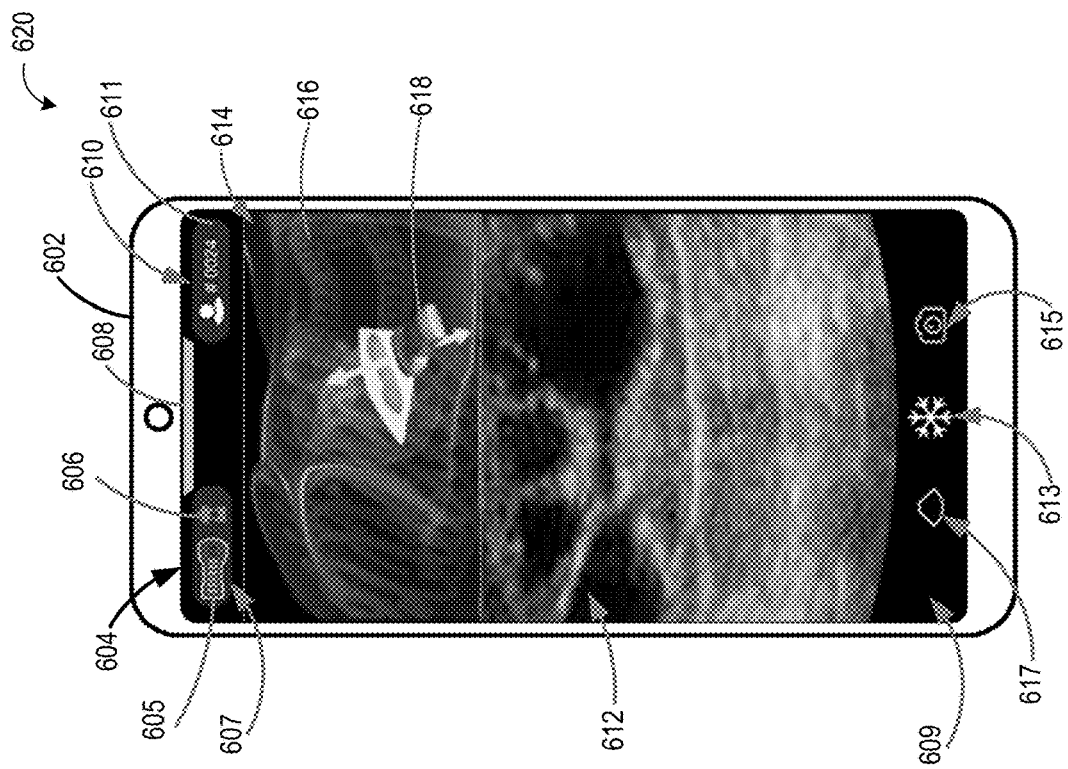

An example ultrasound system including an ultrasound probe, a display device, and a processor are shown in FIG. 1. Via the ultrasound probe, ultrasound images may be acquired and displayed on the display device. The images may be acquired by adjusting the position of the ultrasound probe on a patient's body. To determine if the acquired ultrasound images are of sufficient image quality, the ultrasound images may be compared with reference models that may determine if unsatisfactory (e.g., low) image quality is due to aspects of probe placement, so that guidance may be displayed to aid the user in adjusting the position of the ultrasound probe in order to improve image quality. One or more rubrics may be used to assess and/or score user proficiency on one or more anatomical regions on which the adaptive guidance system has been trained, as shown in FIG. 2. A processor may programmatically determine when and how to display user guidance on a display device during operation of an ultrasound imaging system and track operator proficiency, via example methods illustrated in FIGS. 3A, 3B, and 3C. The user guidance may include contextual guidance, as shown in FIGS. 4A, 4B, and 4C, and/or real-time guidance cues, as shown in 5A and 5B. The user guidance may include superimposed images, text, video, and/or other visual display features, as shown in FIGS. 6A, 6B, 6C, and 6D. Use of the adaptive guidance system may result in increased proficiency scores and faster acquisition of proficiency over time, as shown in FIGS. 7A and 7B, which also depict threshold proficiencies. Thus, by providing a system and methods for displaying contextual and real-time guidance to users of different proficiency levels, patient satisfaction and clinical outcomes may be improved, and significant savings in time and money may be obtained by shortening a learning curve associated with image acquisition.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body of a patient (not shown). The probe 106 may be a one-dimensional transducer array probe, or may be a two-dimensional matrix transducer array probe. The transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. A user interface 115 may be used to control operation of the ultrasound imaging system 100. The user interface 115 may include one or more of the following: a rotary element, a mouse, a keyboard, a trackball, hard keys linked to specific actions, soft keys that may be configured to control different functions, and/or a graphical user interface displayed on a display device 118.

The ultrasound imaging system 100 includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory 120. As discussed herein, memory includes any non-transient computer readable medium in which programming instructions are stored. For the purposes of this disclosure, the term tangible computer readable medium is expressly defined to include any type of computer readable storage. The example methods and systems may be implemented using coded instruction (e.g., computer readable instructions) stored on a non-transient computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include any other medium which can be used to store the desired electronic format of information and which can be accessed by the processor or processors or at least a portion of a computing device.

The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 may be adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

The ultrasound imaging system 100 may include a data processing unit 130 configured to progressively analyze an operator's proficiency in acquiring ultrasound images. As described in further detail below, the operator's proficiency may be assessed with respect to a plurality of proficiency parameters, anatomical regions and/or target anatomical features. For example, the operator may be assigned proficiency scores based on the operator's proficiency in acquiring ultrasound images of a liver, or a spleen, or a uterus, or another part of the human anatomy, where a proficiency score assigned to the operator for acquiring images of a spleen may be different from a proficiency score assigned to the operator for acquiring images of a liver. Further, as described in greater detail below, the proficiency score may be a function (e.g., a summation, an average, a weighted average, etc.) of individual proficiency scores assigned to the operator in regard to individual proficiency parameters (e.g., image quality, acquisition speed, scan plane accuracy, etc.). Similarly, a proficiency score for an anatomical region, or across a plurality of anatomical regions, may be assigned to the operator as a function of the operator's proficiency scores assigned in regard to target anatomical features. For example, the operator may be assigned a proficiency score for the anatomical region of the abdomen, where the score is an average of the operator's proficiency scores on a plurality of target anatomical features of an abdomen (e.g., a liver, a spleen, a uterus, etc.). The operator may also be assigned an overall proficiency score, where the overall proficiency score is a function of the operator's proficiency scores for a plurality of anatomical regions (e.g., abdomen, chest, etc.). In this way, a robust framework is provided for assessing the operator's proficiency at acquiring ultrasound images on various parts of the human anatomy and at various scales.

Analyzing an operator's proficiency may include scoring the operator's performance based on a set of one or more qualitative and quantitative proficiency parameters in accordance with a predefined rubric for measuring proficiency, where the set of one or more qualitative and quantitative proficiency parameters (hereinafter "proficiency parameters") correspond to various evaluation attributes for a selected target anatomical feature. The evaluation attributes may include one or more of image quality, speed of acquisition, accuracy of scan plane, visualization of intended anatomical feature including anomalies, cumulative hours of practice, number of exams, repeatability, and reproducibility. The predefined rubric comprising the set of proficiency parameters corresponding to the various evaluation attributes is referred to herein as a "pre-set", where a pre-set corresponds to a specific target anatomical feature. For example, the operator's proficiency in acquiring images of a uterus may be scored in accordance with a uterus pre-set, whereby the operator's proficiency score for the uterus pre-set is a function of the operator's individual proficiency scores on each one of the set of qualitative and quantitative parameters comprised by the uterus pre-set. Similarly, the operator's proficiency in acquiring images of a liver may be scored in accordance with a liver pre-set, whereby the operator's proficiency score for the liver pre-set is a function of the operator's individual proficiency scores on each one of the set of qualitative and quantitative parameters comprised by the liver pre-set. Pre-sets are described in further detail below, in relation to an example pre-set illustrated in FIG. 2.

The data processing unit 130 may receive as input images generated by the ultrasound probe 106, scan settings information received from the user interface 115, and/or historical information relating to the operator's use of the ultrasound imaging system 100. The historical information may be stored in a proficiency database 132 that is electronically coupled to the processor 116. For example, the proficiency database 132 may store the operator's current and/or previous proficiency scores on one or more pre-sets, the number of ultrasound examinations the operator has carried out for each pre-set, the amount of time spent by the operator performing examinations within and across pre-sets, etc. The output of the data processing unit 130 may be a new proficiency score and/or an updated proficiency score (e.g. on a pre-set, or across a collection of pre-sets), which may be stored in the proficiency database 132 as described above. As described in further detail below in reference to FIGS. 3A and 3B, the proficiency score may be used to determine whether to display user guidance and/or specify what type of user guidance may be displayed.

The evaluation attributes corresponding to the proficiency parameters represent criteria used for proficiency assessments. The evaluation attributes may include an accuracy of a scan plane. In one example, scan plane accuracy may be assessed based on a comparison of the images being acquired with one or more reference images by an AI algorithm. In addition, the metrics for scan plane accuracy may take into account if a "standard cross sectional view" of an organ was achieved that is widely used in practice to perform visualization, measurements and reporting such as a long axis view, a short axis view or a 4 chamber view of the whole heart, or a cross section of the whole kidney through a longitudinal plane or a transverse plane etc., which may determine the accuracy of measurements and quality of visualization. Further, the AI algorithm in conjunction with probe marker orientation information may be used to detect any erroneous Left/Right inversion of the image displayed]]. For example, the AI algorithm may provide an assessment of scan plane accuracy by determining whether a number of anatomical features are present in the image, and/or whether the anatomical features in an image exceed a threshold visibility (e.g., resolution.). The AI algorithm may also evaluate one or more anatomical feature parameters in the image including shape of the anatomical features in determining the scan plane accuracy In another example, the AI algorithm may provide an assessment of scan plane accuracy by identifying anatomical features in an image and comparing distance ratios between the anatomical features with distance ratios between the same anatomical features of a reference image, or by comparing the relative scale of anatomical features in an image with the scale of same anatomical features of a reference image. It should be appreciated that the examples provided herein are for illustrative purposes, and other criteria and/or algorithms may be used by the data processing unit 130 for proficiency assessment without departing from the scope of this disclosure.

The evaluation attributes may include image quality. For example, the quality of an image may include evaluating criteria such as image contrast, contrast-to-noise ratio, spatial resolution, grayscale mapping, etc. Additionally or alternatively, image quality may be evaluated based on comparison with one or more reference images in a corresponding scan plane. In addition to the above, other image quality attributes include adequacy of acoustic coupling (with gel) and contact pressure at the probe tip, any image artifacts due to air pockets, foreign objects, shadow of bony structure or motion artifacts in moving organs (as in case of the heart, fetus, lungs etc.) or artifacts due to bowel gases that define the imaging outcomes and in turn the user's proficiency. In this way opportunities for false-positive or false-negative reporting as a result of poor image acquisition may be reduced.

The evaluation attributes may include speed of acquisition. For example, the data processing unit may compare a duration of time taken by the operator in acquiring an image of a desired quality with a pre-defined reference duration indicative of a proficiency level, and assign the operator a proficiency score as a function of the difference between the operator's acquisition speed and the reference acquisition speed.

The evaluation attributes may include accumulated information, such as cumulative hours of practice, number of exams performed on a given pre-set, an assessment of repeatability and/or reproducibility, etc. For example, repeatability and reproducibility may be assessed by determining a relative positioning of anatomical features in an image, and comparing a first standard deviation between the relative positioning of the anatomical features in an acquired image with a second standard deviation between the relative positioning of the anatomical features in images previously acquired by the operator under the same conditions (e.g., repeatable during the same examination, with the same subject, etc.) and under different conditions (e.g., reproducible from a different examination, with a different subject, etc.), respectively. Said another way, consistently in the user's ability to visualize an organ/anatomy of an individual subject multiple times during an exam may be utilized in determining repeatability, while consistency in the user's ability to visualize the same organ/anatomy from different individuals in successive exams may be utilized in determining reproducibility. An operator who demonstrates an ability to repeatedly and reproducibly acquire an image of a desired image quality and scan plane accuracy within a threshold duration may be assigned a higher proficiency score than an operator who is unable to repeatedly and reproducibly acquire a suitable image within a threshold duration.

As described in more detail below, the pre-defined rubric may progressively yield updated proficiency scores of an operator, which may be used to dynamically determine whether user guidance for a specified pre-set may or may not be displayed to the operator on the display device 118 during workflow. For example, the system may determine whether a current proficiency score of the operator for various pre-sets is lower than a threshold proficiency value in order to selectively enable displaying user guidance.

User guidance for a specified pre-set may also be displayed if the operator is taking an amount of time to obtain a desired quality image that exceeds a threshold duration. For example, if an operator is attempting to acquire ultrasound images of a heart and does not achieve a target scan plane (e.g., a scan plane in which a specific set of anatomical features are visible) within a pre-defined threshold duration for a heart pre-set, the ultrasound system 100 may display one or more forms of user guidance on the display device 118 to aid the operator in achieving the target scan plane. Further, a duration for waiting prior to displaying the graphical user guidance (e.g., before it is turned ON) may be predefined (e.g., programmed into instructions in a memory such as memory 120) or adjusted dynamically based on one or more criteria. For example, a waiting period prior to displaying user guidance may be predefined at 60 seconds by default, and/or the duration may be reduced to 30 seconds if the operator is assigned a proficiency score below a given threshold proficiency score. There may also be an additional manual override to control the ON/OFF state of the user guidance such that an operator may opt to hide the user guidance, for example, if the operator determines that the user guidance is not helpful.

The user guidance may be contextual guidance in the form of reference images and/or real-time guidance, in the form of cues, textual instructions or display elements that indicate how a position, orientation, or pressure of the ultrasound probe 106 may be adjusted to acquire images of a desired quality. The contextual guidance may include a reference ultrasound image, which may be a high-quality ultrasound image pre-acquired by an experienced sonologist or radiologist from an earlier patient. The reference ultrasound image may be acquired from a person being currently examined based on an AI algorithm running in real-time. For example, if an operator acquires a plurality of images from various scan planes when attempting to position the ultrasound probe 106 to acquire images within a target scan plane, an AI algorithm may determine that one of the images acquired is in the target scan plane and display that image on the display device 118 as a reference image, or alternatively display a "target acquired" indication. As another example, contextual guidance may include an anatomical illustration, pre-recorded training video, or a video of a remote assistant connected via a video conference, and real-time guidance may include display elements generated by the remote assistant connected through a video call. The guidance cues may include prompts, check-lists of protocol steps, and/or any other kind of graphical display elements. In other embodiments, the user guidance may be displayed in conjunction with one or more peripheral devices such as, for example, an external camera to support eye-tracking capability. It should be appreciated that the examples of user guidance provided herein are for illustrative purposes, and other types of user guidance may be included without departing from the scope of this disclosure.

In this way, as an operator acquires images while performing an ultrasound exam, customized guidance may be generated that includes the display of graphical, visual, or textual elements, concurrent with the visual images being acquired, for operators with varied capabilities and/or different levels of experience, such that guidance may be provided in an adaptive manner in accordance with the operator's progressively evolving proficiency without relying on a consciously managed configuration selected by the operator. This addresses the problem of matching guidance to a proficiency level, meaning, and the problem of directing guidance to operators of different proficiency levels such that expert operators are not distracted by user guidance that is not helpful, while novice users are not deprived of helpful guidance. A further advantage of the ultrasound system disclosed herein is that it does not rely on additional hardware, and the costs associated with enabling the disclosed features are minimal, thereby enhancing techno-commercial feasibility and increasing the adoption of ultrasound imaging among non-traditional users including urologists, gynaecologists, and/or other clinicians.

Turning now to FIGS. 2A, 2B, and 2C, an example pre-set for assessing the proficiency of a user of an ultrasound imaging system is shown. Pre-set chart view 200 of FIG. 2A shows general rubric for determining a proficiency score of a user for any anatomical region or structure. Pre-set chart view 230 of FIG. 2B shows an example rubric for determining a proficiency score of a user for a liver pre-set. Pre-set chart view 260 of FIG. 2C shows example weightings, level scores, user scores, and proficiency score of a user for a liver pre-set. The ultrasound imaging system may be the same as, or similar to, the ultrasound imaging system 100 of FIG. 1. It should be appreciated that while the pre-set chart views 200, 230, and 260 illustrate the features of a pre-set and an underlying rubric for assessing proficiency, the data shown in each of the pre-set chart views 200, 230, and 260 may not be stored in a single table format, and may be stored in a relational database in accordance with a different data structure and/or across various database tables in relation to an operator of the ultrasound imaging system. The relational database may be the same as or similar to the proficiency database 132 of the ultrasound imaging system 100 of FIG. 1.

Referring now to FIG. 2A, pre-set chart view 200 is shown, which illustrates a rubric or framework for determining a proficiency score of a user of the ultrasound imaging system. The pre-set chart 200 may be categorized according to an anatomical region, as indicated by the anatomical region label 202. For example, the pre-set chart 200 may relate to ultrasound examinations performed in the anatomical region of the abdomen, chest, etc. The pre-set chart 200 may further relate to a specific anatomical target, as indicated by the anatomical target label 204. For example, the pre-set chart 200 may relate to ultrasound examinations performed on a liver, spleen, heart, etc. The pre-set chart 200 may include one or more proficiency parameters 206, shown in the left-hand column of the pre-set chart 200 in FIG. 2A, which may represent different components into which a proficiency of the operator of the ultrasound system may be individually assessed. The proficiency parameters 206 may include image suitability criteria, such as image quality and/or scan plane accuracy. The proficiency parameters 206 may include a speed of the operator in acquiring ultrasound images of a desirable quality. The proficiency parameters 206 may also include historical information, such as a number of practice hours completed, a number of ultrasound exams completed, and/or an assessment of the reproducibility and/or repeatability of an ultrasound procedure by the operator. For example, a high reproducibility score may be assigned to an operator who performs a plurality of ultrasound exams, where a standard deviation between level scores associated with parameters such as image quality, scan plane accuracy, and acquisition speed for each ultrasound exam are below a threshold value.

For each proficiency parameter 206, a user score 210 may be generated that reflects the proficiency of the user on the proficiency parameter. In an embodiment, the user score 210 may be a summation, for a corresponding proficiency parameter 206, of one or more level scores 208, where each of the one or more level scores 208 assesses the proficiency of the operator within the relevant level. In one example, an operator may be assigned a level score 208 for each of level 1, level 2, and level 3 in relation to a given proficiency parameter 206. The level scores may be summed to generate a user score 210 for the proficiency parameter 206. In other examples, the user score 210 may be assigned as a different function of the operator's level scores 208. For example, the user score 210 may be an average of the operator's level scores 208. Further, the determination of the user score 210 may be based on a weighting of the level scores 208, where a summation, average, etc. of the level scores are multiplied by a weight 212 associated with the relevant proficiency parameter. For example, the proficiency parameter image quality may have a weight 212 of 0.9 associated with it, where an average of the level scores are multiplied by 0.9 to generate a weighted user score 210 for the proficiency parameter image quality. The weight 212 associated with each proficiency parameter 206 may be different, whereby the weight 212 may reflect a relative importance of the proficiency parameter 206 in relation to other proficiency parameters 206. In still other examples, a level score for level 1 may be weighted more than a level score for level 2, or a level score for level 3 may be weighted more than a level score for level 2 for the proficiency parameter of image quality, while a level score for level 3 may be weighted less than a level score for level 2 for the proficiency parameter of reproducibility, etc.

The user scores 210 may be further combined to generate a proficiency score 216 that reflects a proficiency of the operator on a preset. For example, an operator may be assigned a first proficiency score for a liver preset that reflects the proficiency of the operator in acquiring images of a liver, and the operator may be assigned a second proficiency score for a kidney preset that reflects the proficiency of the operator in acquiring images of a kidney. In this way, a plurality of proficiency scores may be generated for the operator that reflect an overall proficiency of the operator across a plurality of anatomical regions and a plurality of anatomical targets. Further, in some examples, an overall proficiency score may be determined as a function of the plurality of proficiency scores generated for the operator. In one example, the proficiency score 216 may be a number between 0 and 1 (e.g., 0.9). In other examples, the proficiency score 216 may be a number between 0 and 100 (e.g., 85), or the proficiency score 216 may be a number that is unbounded.

The level scores 208 may be based on quantitative and/or qualitative criteria, depending on the parameter. For example, a level score 208 for acquisition speed may be based on quantitative criteria (e.g., a duration) and not on qualitative criteria. Alternatively, a level score 208 for image quality may be based on either qualitative and quantitative criteria, or a combination of qualitative and quantitative criteria. Qualitative criteria for image quality may include, for example, whether an entire structure was imaged, whether the user has frozen on an optimal image of a sequence of images, a suitability of a scan plane for viewing an organ, whether any features are missing from an acquired image, and so forth. Quantitative criteria for image quality may include, for example, how many nodules, tumor sites, etc. have been captured out of a total number of nodules, tumor sites, etc., or how many features of an anatomical structure are captured. Examples of qualitative and quantitative criteria are provided below in relation to FIG. 2B, and example level and user scores are provided below in relation to FIG. 2C.

In some examples, each of the level scores 208 may provide an assessment of the operator's proficiency in acquiring ultrasound images of a different level of difficulty. Under each level and for each proficiency parameter 206, a qualitative and/or quantitative criteria may be specified as to what is expected of the operator to get to a particular level for a given anatomical region and anatomical structure within the anatomical region. Based on whether or not the criteria are satisfied, the user score 210 may be computed. In one example, the level scores 208 are binary, reflecting either a passing score for a level (e.g., 1.0) or a failing score for a level (e.g., a 0.0). For example, an operator may receive a level score 208 of 1.0 for level 1 for the proficiency parameter image quality, indicating that the operator has met one or more image quality criteria associated with a level 1 operator. However, the operator may receive a level score 208 of 0.0 for level 2 for the proficiency parameter image quality, indicating that the operator has not met one or more image quality criteria associated with a level 2 operator. As a result, it may be interpreted that for image quality, the operator has passed level 1, but has not passed level 2. A user score 210 may then be generated for the operator, where the user score is the result of multiplying the level score of 1.0 for level 1 by a weight 212 associated with the proficiency parameter image quality. An example for an anatomical target (e.g., a liver) is described below in reference to FIGS. 2B and 2C.

In other examples and/or for some quantitative proficiency parameters 206, such as number of practice hours or number of exams completed, the level score 208 associated with the proficiency parameter 206 may be a different type of score than a type of score used for other proficiency parameters 206 (e.g., qualitative proficiency parameters). For example, a level score for the proficiency parameter of number of practice hours may be the actual number of hours completed, while a level score for the proficiency parameter of image quality may be a score from 1 to 10, where 1 is the lowest score and 10 is the highest score. Further, the user score 210 may not be the same type of score as a level score for the same proficiency parameter 206. For example, a user score for the proficiency parameter of practice hours may be a score generated as a function of one or more level scores indicating a number of hours completed. For example, if the user scores for each proficiency parameter 206 are values between 1 and 10, with 10 representing high proficiency and 1 representing low proficiency, an operator who has completed a total of 60 hours of practice across all levels of a given pre-set may be assigned a user score of 8 (e.g., a high score reflecting high proficiency) based on a pre-established mapping function, while an operator who has completed a total of 5 hours of practice across all levels of the pre-set may be assigned a user score of 1 (e.g., a low score reflecting low proficiency). The scores of the pre-set chart 200 may be updated each time an operator performs an ultrasound exam with the ultrasound imaging system. For example, as the number of ultrasound exams that an operator performs increases, the proficiency parameters of number of exams and/or number of practice hours may be incremented. The operator's level scores 208 and/or user scores 210 may be adjusted to reflect changes in the operator's proficiency over time. For example, an operator who has achieved a passing level score 208 for Level 1 corresponding to a proficiency parameter of scan plane accuracy may be assigned a new passing level score 208 for Level 2, reflecting that the operator has developed an increased proficiency in acquiring images within a target scan plane. Alternatively, after completing the same exam, a level score 208 of the operator corresponding to a proficiency parameter of image quality may not increase as the number of practice hours increases, reflecting that the operator's increased proficiency in adjusting the ultrasound probe to acquire images within a target scan plane does not translate into an increased ability to generate high quality images (e.g., because different skills may be involved). The pre-set chart 200 may also be updated periodically to reflect changes in the underlying proficiency rubric. For example, additional proficiency parameters 206 may be added, removed, combined, or split into two or more new proficiency parameters 206.

Referring now to FIG. 2B, an example liver pre-set chart view 230 is shown, where the liver pre-set chart view 230 is an example of the pre-set chart view 200 of FIG. 2A specific to an anatomical target of a liver, as shown in the anatomical region label 202 and the anatomical target label 204. In liver pre-set chart view 230, example criteria specific to a liver preset are provided for each proficiency parameter 206. In one example, for the proficiency parameter of image quality, an example criterion for passing level 1 is that the operator is able to visualize a structure of a target anatomical feature, while an example criterion for passing level 5 is that the operator is able to visualize a structure of a target anatomical feature, and that the operator is able to visualize an entire organ of the target anatomical feature within a duration of less than 1 minute. Criteria for levels 2, 3, and 4 may include one or more intermediate quality thresholds, where if the operator acquires images above the one or more intermediate quality thresholds, then the operator passes the relevant level.

As other examples, example criteria for the proficiency parameter of acquisition speed may include a threshold duration for each level. For example, the operator may be assigned a passing score for level 1 if the operator is able to acquire a suitable image within 3 minutes, the operator may be assigned a passing score for level 2 if the operator is able to acquire a suitable image within 2.5 minutes, the operator may be assigned a passing score for level 3 if the operator is able to acquire a suitable image within 2 minutes, and so on. Example criteria for the proficiency parameter of scan plane accuracy may include different qualitative and/or quantitative criteria for levels 1-5, for example, the operator may be assigned a passing score for level 1 if the operator is able to identify a target scan plane, and the operator may be assigned a passing score for level 2 if the operator is able to identify a target scan plane and adjust an ultrasound probe accordingly, while passing scores for levels 3, 4, and 5 may be assigned based on a duration taken by the operator to acquire a scan plane accurately. Criteria for levels 1-5 for the proficiency parameters of number of practice hours and number of exams may include achieving a threshold number of practice hours and achieving a threshold number of exams. For example, the operator may be assigned a level score of 1.0 for level 1 for the proficiency parameter of number of practice hours if the operator achieves more than four practice hours, the operator may be assigned a level score of 1.0 for level 2 for the proficiency parameter of number of practice hours if the operator achieves more than six practice hours, and so on. For the proficiency parameters of reproducibility and repeatability, the operator may be assigned a level score based on a duration taken to acquire an image reproducibly (e.g., images of the same target anatomical feature from different subjects) or a duration taken to acquire an image repeatedly (e.g., images of the same target anatomical feature from the same subject under the same conditions).

As described above in relation to FIG. 2A, a weight 212 may be associated with each proficiency parameter 206. For example, the proficiency parameter of image quality may have a weight of 1.0, the proficiency parameter of acquisition speed may have a weight of 0.7, the proficiency parameter of scan plane accuracy may have a weight of 0.9, the proficiency parameter of number of practice hours may have a weight of 0.05, the proficiency parameter of number of exams may have a weight of 0.6, the proficiency parameter of reproducibility may have a weight of 0.3, and the proficiency parameter of repeatability may have a weight of 0.3. Further, the weights of the proficiency parameters may indicate a relative importance of a proficiency parameter with respect to other proficiency parameters. For example, the weight 1.0 assigned to the proficiency parameter of image quality may indicate that image quality is of greater relative importance in generating a proficiency score 216 than a number of practice hours, which is assigned a weight of 0.5 (e.g., the number of practice hours achieved by the operator may be less indicative of a proficiency of the operator than an ability of the operator to achieve an image of a desired quality).

Further still, some levels of a pre-set may be more important than other levels of the pre-set. For example, as shown by bold lines 232 and 234, level 1 may considered more important (e.g., a bigger milestone towards achieving a high proficiency) than levels 2, 3, and 4, which may represent smaller milestones towards achieving a high proficiency). The proficiency gap may not be "even" between any two successive levels and therefore a differential priority may be considered by using the bold lines, as indicated above.

Turning now to FIG. 2C, an example liver pre-set chart view 260 is shown, where the liver pre-set chart view 260 is an example of the pre-set chart view 200 of FIG. 2A specific to an anatomical target of a liver. In liver pre-set chart view 260, example weights 212, level scores 208, user scores 210, and an example proficiency score 216 are shown, where the example user scores 210 are calculated as a weighted summation of the level scores 208, and the proficiency score 216 is calculated based on a summation of the user scores 210. The level scores 208 shown under the columns of Level 1-Level 5 may correspond to the qualitative and quantitative criteria for each proficiency parameter 206 and each level.

For example, a level score of 1.0 under Level 1 for the proficiency parameter image quality may indicate that an operator has fulfilled the criterion of being able to visualize a target structure shown in the example liver pre-set chart view 230 of FIG. 2B under Level 1 for the proficiency parameter image quality. Similarly, a level score of 1.0 under Level 1 for the proficiency parameter acquisition speed may indicate that the operator has fulfilled the criterion of acquiring a suitable image within 3 minutes shown in the example liver pre-set chart view 230 of FIG. 2B under Level 1 for the proficiency parameter acquisition speed; a level score of 1.0 under Level 1 for the proficiency parameter scan plane accuracy may indicate that the operator has fulfilled the criterion of identifying a target scan plane shown in the example liver pre-set chart view 230 of FIG. 2B under Level 1 for the proficiency parameter scan plane accuracy; a level score of 1.0 under Level 1 for the proficiency parameter number of practice hours may indicate that the operator has fulfilled the criterion of exceeding 4 hours of practice time shown in the example liver pre-set chart view 230 of FIG. 2B under Level 1 for the proficiency parameter number of practice hours; a level score of 1.0 under Level 1 for the proficiency parameter number of examinations may indicate that the operator has fulfilled the criterion of exceeding 5 hours of exams shown in the example liver pre-set chart view 230 of FIG. 2B under Level 1 for the proficiency parameter number of exams; a level score of 1.0 under Level 1 for the proficiency parameter reproducibility may indicate that the operator has fulfilled the criterion of achieving a target scan reproducibly across different subjects within 60 seconds shown in the example liver pre-set chart view 230 of FIG. 2B under Level 1 for the proficiency parameter reproducibility; and a level score of 1.0 under Level 1 for the proficiency parameter repeatability may indicate that the operator has fulfilled the criterion of achieving a target scan repeatedly on the same subject during the same exam within 60 seconds shown in the example liver pre-set chart view 230 of FIG. 2B under Level 1 for the proficiency parameter repeatability.

In example liver pre-set chart view 260, the operator has level scores of 1.0 for the proficiency parameters 208 of Level 1 and Level 2, indicating that the operator has passed Level 2 based on the criteria shown in example liver pre-set chart view 230. Pre-set chart view 260 further shows that the operator has a level score of 1.0 under Level 3 for the proficiency parameter of image quality, a level score of 1.0 under Level 3 for the proficiency parameter of scan plane accuracy, and a level score of 1.0 under Level 3 for the proficiency parameter of repeatability. As a result, it may be concluded that the operator has achieved an image quality that meets a desired threshold quality associated with Level 3, a scan plane accuracy that meets a desired threshold accuracy associated with Level 3, and a repeatability that meets a desired threshold repeatability associated with Level 3. However, the operator has a level score of 0.0 under Level 3 for the proficiency parameters of acquisition speed, scan plane accuracy, and repeatability, indicating that the operator has not yet met one or more criteria for the proficiency parameters of acquisition speed, scan plane accuracy, and repeatability under Level 3. For example, it may be concluded that the operator has not practiced enough and/or been exposed to a sufficient number of exams to achieve a desired acquisition speed and reproducibility to pass Level 3, while the operator may have a high degree of natural ability in acquiring images.

As described above, a user score 210 may be calculated for the operator as a function of the level scores 208 and the weights 212. In one example, the user scores 210 are calculated as a weighted summation of the level scores 208 for each proficiency parameter. For example, the operator may be assigned a user score of 3.0 for the proficiency parameter image quality, reflecting a summation of the level score of 1.0 under level 1, the level score of 1.0 under level 2, the level score of 1.0 under level 3, the level score of 0.0 under level 4, and the level score of 0.0 under level 5, which is then multiplied by the weight 1.0 associated with the proficiency parameter image quality. Similarly, the operator may be assigned a user score of 1.8 for the proficiency parameter acquisition speed, reflecting a summation of the level score of 1.0 under level 1, the level score of 1.0 under level 2, the level score of 0.0 under level 3, the level score of 0.0 under level 4, and the level score of 0.0 under level 5, which is then multiplied by the weight 0.9 associated with the proficiency parameter image quality. User scores for the remaining proficiency parameters shown in FIG. 2C (scan plane accuracy, number of practice hours, number of exams, reproducibility, and repeatability) are calculated in the same fashion, yielding user scores for each proficiency parameter as shown in the user score column of FIG. 2C.

Further, a proficiency score 216 may be calculated based on the user scores 210, which may reflect an overall proficiency of the operator across a plurality of proficiency parameters. In one example, the proficiency score 216 may be calculated as a summation of the user scores for the proficiency parameters image quality, acquisition speed, scan plane accuracy, number of practice hours, number of exams, reproducibility, and repeatability. In other examples, the proficiency score 216 may be calculated as an average of the user scores for the proficiency parameters image quality, acquisition speed, scan plane accuracy, number of practice hours, number of exams, reproducibility, and repeatability, or a different function of the user scores for the proficiency parameters image quality, acquisition speed, scan plane accuracy, number of practice hours, number of exams, reproducibility, and repeatability. In still other examples, the proficiency score 216 may be calculated as a function of the user scores for a smaller number of proficiency parameters. For example, the proficiency score 216 of an expert operator may be calculated as a function of the user scores for the proficiency parameters image quality, acquisition speed, scan plane accuracy, reproducibility, and repeatability, but not for the proficiency parameters number of practice hours or number of exams. It should be appreciated that the examples provided herein are for illustrative purposes, and other functions and/or methods for calculating the user score 210 or the proficiency score 216 may be included without departing from the scope of this disclosure.

Thus, a plurality of pre-set charts 200 may be associated with a single user of an ultrasound imaging system, where each of the plurality of pre-set charts 200 represents a rubric for assigning a proficiency score to the operator in reference to the operator's performance of an ultrasound exam for the anatomical target associated with the pre-set chart 200. In some embodiments, an operator's total experience in performing ultrasound examinations on a given pre-set (e.g., a liver pre-set) may be measured by assigning a pre-set proficiency score to the operator, where the pre-set proficiency score is a function of the operator's individual user scores 210 for each proficiency parameter 206. Further, an operator's overall experience in performing ultrasound examinations across all available pre-sets may be measured by assigning an overall proficiency score to the operator, where the overall proficiency score may be a function of the operator's pre-set proficiency scores on each of the plurality of pre-set charts 200. In this way, a collection of pre-sets represents a structure or framework for capturing and tracking the evolution of the ultrasound operator's proficiency as the operator gains experience over time, broken down by target anatomical feature, with respect to various criteria. This framework provides a basis for automated guidance to be provided to an ultrasound operator in accordance with the operator's abilities in order to facilitate an increase in the operator's proficiency in acquiring ultrasound images. Further, the proficiency scores captured in the pre-sets may be leveraged such that the type, style, and/or amount of automated guidance may be adjusted based on the operator's proficiency scores.

For example, when an operator logs into an ultrasound imaging system (e.g., the ultrasound imaging system 100 of FIG. 1) to perform an ultrasound examination of a patient's liver, a processor of the ultrasound imaging system (e.g., the processor 116 of the ultrasound imaging system 100 of FIG. 1) may request from a database (e.g., the proficiency database 132 of the ultrasound imaging system 100 of FIG. 1) a proficiency score of the operator in accordance with a liver pre-set. The operator's proficiency score on the liver pre-set reflects the operator's proficiency in administering ultrasound exams of livers, based on the operator's experience and skill level as described above. If the operator's proficiency score for the parameter of scan plane acquisition is low (e.g., below a threshold value), the processor may display visual guidance cues on a display device of the ultrasound system (e.g., the display device 118 of the ultrasound system 100 of FIG. 1) to aid the operator in achieving the right scan plane for acquiring images of relevant features of the patient's liver. The visual guidance cues may include, by way of illustration, one or more display elements (e.g., an arrow, a symbol, etc.) indicating a direction of and/or amount of pressure to apply to the probe and/or a direction to which to adjust a position of the probe, textual instructions to adjust one or more scan settings of the ultrasound imaging system, etc. The guidance cues may be displayed in conjunction with a pre-established reference ultrasound image of a liver in the target scan plane, which the operator may compare to the images being acquired, or a textbook illustration of a liver with annotated information, or a 3D model of a liver, or reference images of a different kind. It should be appreciated that the examples provided herein are for illustrative purposes and any type of guidance cues may be included without departing from the scope of this disclosure.

The user guidance may include contextual guidance in the form of reference images, such as pre-acquired reference ultrasound images, anatomical illustrations, etc. Contextual user guidance may also include high-quality ultrasound images pre-acquired by an experienced sonologist/radiologist from an earlier patient, or images generated by a remote assistant connected through a video call. The user guidance may also include real-time guidance, in the form of cues for probe placement and/or orientation (e.g., graphical display elements such as arrows, lines, indicators, etc.), textual instructions, prompts or check-lists of protocol steps, and so forth. The real-time guidance and/or the contextual guidance may be displayed in conjunction with or superimposed upon images acquired in real time by the ultrasound probe. The real-time guidance may also be displayed in conjunction with or superimposed upon the contextual guidance (e.g., reference images), which in turn may be displayed in conjunction with or superimposed upon images acquired in real time by the ultrasound probe. In this way, different forms of contextual and real-time user guidance may be combined and displayed dynamically in conjunction with the images being acquired by the ultrasound probe, in accordance with one or more AI algorithms.

The processor may also leverage an operator's proficiency scores to determine a duration for which to display user guidance. Returning to the example above, the processor may display user guidance to an operator with a low proficiency score in acquisition speed on a liver pre-set earlier (e.g., after a shorter waiting period) than an operator with a high proficiency score in acquisition speed on a liver pre-set. Similarly, the processor may stop displaying guidance to an operator with a low proficiency score in acquisition speed on a liver pre-set later than an operator with a high proficiency score in acquisition speed on a liver pre-set. The displaying and timing of user guidance by the processor is described in more detail below in reference to FIGS. 3A and 3B. Referring now to FIG. 3A, a flowchart illustrates an example method 300 for displaying user guidance to a user on an ultrasound display device, based on a proficiency score of the user and/or a selection of the user. Method 300 is described with regard to the systems and components of FIG. 1, though it should be appreciated that the method 300 may be implemented with other systems and components without departing from the scope of the present disclosure. Method 300 may be carried out by a processor, such as the processor 116 of the ultrasound imaging system 100 of FIG. 1, in accordance with instructions stored in non-transitory memory of a computing device, such as memory 120 of ultrasound imaging system 100 of FIG. 1.

At 302, an ultrasound operator logs into an ultrasound system using login credentials, and method 300 includes initiating operation of the ultrasound system with the login credentials of the operator. At 304, method 300 includes prompting the operator to select a desired pre-set/anatomy of interest to begin scanning. The pre-set may be the same as, or similar to, the pre-set described by pre-set charts 200, 230, and 260 of FIG. 2. Once the operator selects the appropriate pre-set for the ultrasound examination, the pre-set is loaded into a memory of the ultrasound imaging system (e.g., the memory 120 of FIG. 1), whereby the processor may access the operator's proficiency scores on the selected pre-set, and scanning is initiated by the operator.

The ultrasound images may be acquired with an ultrasound probe (e.g., the ultrasound probe 106 of ultrasound imaging system 100 of FIG. 1) and displayed to an operator via a display device (e.g., the display device 118 of ultrasound imaging system 100 of FIG. 1). The images may be acquired and displayed in real time or near real time, and may be acquired with default or user-specified scan parameters (e.g., default depth, frequency, etc.). The ultrasound images may be acquired as part of an ultrasound exam where certain anatomical features are imaged in certain views/axes in order to diagnose a patient condition, measure aspects of the anatomical features, etc. As an example, during a cardiac exam, one or more target scan planes (also referred to as views) of the heart of a patient may be imaged. The target scan planes may include a four-chamber view, a two-chamber view (which may also be referred to as a short axis view), and a long axis view (which may also be referred to as a PLAX view or three-chamber view.

At 306, method 300 includes accessing the last saved proficiency score for the current pre-set from a database (e.g., the database 132 of ultrasound imaging system 100 of FIG. 1). In an embodiment, the proficiency score may be displayed on the display device such that the proficiency score is visible to the operator. In other embodiments, the proficiency score may not be displayed, or may be displayed upon request by the operator. The proficiency score may be dynamically updated. For example, the operator's proficiency score on a pre-set may increase as the proficiency parameter of practice hours increases, or the operator's proficiency score on the pre-set may increase as a result of achieving a higher proficiency score than the operator's previous proficiency scores for the proficiency parameter of acquisition speed (e.g., representing faster acquisition speed), or another proficiency parameter.

At 308, method 300 includes generating real-time user guidance based on real-time image acquisition via an AI algorithm. For example, The AI algorithm may be running continuously whether the user guidance is turned ON or OFF. In one example, the AI algorithm may be utilized to monitor how a user is performing during the current exam to determine if and when the use guidance can be turned ON. In another example, adaptive user guidance based on user proficiency may be disabled consciously by the user by using a set-up utility and in that case the AI algorithm that is used to generate a graphical interface of the real-time guidance may stop running till such time the user does not turn it ON manually. Thus the real-time guidance feature may be enabled as a default option or a manually activated option. In some examples, the AI algorithm based on which the graphical interface of real-time guidance may be enabled prior to user's log (that is, prior to step 302). In some embodiments, the AI algorithm may be a rules-based expert system, in which different forms of user guidance (e.g., contextual guidance and/or real-time guidance cues) are generated as appropriate for the operator based the application of one or more rules within a decision tree structure. In other embodiments, the AI algorithm may be a machine learning algorithm.

For example, if a user's proficiency score (e.g., the proficiency score 216 of pre-set charts 200, 230, and 260 of FIG. 2) is below a first threshold value, then the AI algorithm may generate user guidance intended for helping a novice ultrasound operator. If the user's proficiency score is below a second threshold value, then the AI algorithm may generate user guidance intended for helping an intermediate ultrasound operator. If the user's proficiency score is below a third threshold value, then the AI algorithm may generate user guidance intended for helping an advanced ultrasound operator, and so forth.

In some examples, user guidance may be displayed based on a parameter-specific proficiency score (e.g., the user score 210 of pre-set charts 200, 230, and 260 of FIG. 2). For example, if a user's score on the proficiency parameter of image quality is below a threshold quality (e.g., a target structure is not fully visualized, etc.), and the user's score on the proficiency parameter of number of practice hours is below a threshold number of hours, then the AI algorithm may generate user guidance intended for helping a novice ultrasound operator improve image quality. As another example, if the user's score on the proficiency parameter of acquisition time is below a threshold value, and the user's score on the proficiency parameter of number of practice hours is above a threshold value, then the AI algorithm may generate guidance cues intended to aid a more experienced ultrasound operator reduce acquisition time. Thus, an AI algorithm may generate, enable, and/or disable different forms of user guidance based on a combination of factors, including proficiency scores or scores associated with individual proficiency parameters (e.g., the user scores 210 of FIG. 2).

At 310, method 300 includes determining whether a proficiency score of the user exceeds a minimum threshold score. In one example, the ultrasound system may be initialized to establish a baseline proficiency score of the user. The baseline proficiency score may be determined based on the user's credentials, including qualifications and prior experience with ultrasound imaging. Subsequently, after the desired pre-set and/or anatomy of interest for the current exam has been determined, as discussed at step 306, the user's proficiency for the desired pre-set and/or anatomy is determined. Thus, at 310, the method may include determining if the proficiency score for the desired pre-set and/or the anatomy of interest is greater than the minimum threshold score for the desired pre-set and/or anatomy of interest. If the proficiency score of the user does not exceed a minimum proficiency score at 310 (e.g., if the user is a novice operator), then method 300 proceeds to 316. At 316, method 300 includes displaying the user guidance generated at 308 on a display device of the ultrasound system (e.g., the display device 118 of ultrasound imaging system 100 of FIG. 1), thereby ensuring that low proficiency users are provided guidance.

If the proficiency score of the user does exceed a minimum proficiency threshold score at 310, method 300 proceeds to 312. At 312, method 300 includes prompting the user whether to receive guidance, and receiving a response. Proceeding to 314, method 300 includes determining whether the user opts for guidance to be displayed on the device screen. If the user opts for guidance to be displayed on the display device at 360, method 300 proceeds to 316. At 316, method 300 includes displaying the user guidance generated at 308 on the display device. The user guidance may include real-time user guidance and/or contextual user guidance, for example. If the user does not opt for guidance to be displayed on the device screen at 314, method 300 proceeds to 318. At 318, method 300 includes prompting the user whether to exit the pre-set (e.g., at the completion of the examination). At 320, method 300 includes determining whether the user wishes to exit the current pre-set. If the user does not wish to exit the current pre-set at 320, method 300 proceeds back to 308, and user guidance continues to be generated dynamically based on real-time image acquisition via an AI algorithm as described above. Alternatively, if the user wishes to exit the current pre-set at 320 (e.g., once the ultrasound examination has been completed), method 300 proceeds to 322.

In some embodiments, when the proficiency score for the user is greater than the threshold score, a lesser amount of user guidance may be provided; and when the proficiency score for the user is less than the threshold score, a greater amount of user guidance may be provided. The lesser amount of user guidance may include a lesser amount of real-time guidance or a lesser amount of contextual guidance or a lesser amount of real-time and contextual guidance. Likewise, the greater amount of user guidance may include a greater amount of real-time guidance, or a greater amount of contextual guidance, or a greater amount of real-time and contextual guidance. In some examples, the greater amount of real-time guidance may include a maximum amount of real-time and/or contextual guidance.

In some embodiments, more than one proficiency threshold may be applied. As a non-limiting example, when the user's proficiency score is less than a first threshold, a greater amount of user guidance may be provided; when the user's proficiency score is greater than the first threshold but less than the second threshold, a lesser amount of user guidance may be provided; and when the user's proficiency score is greater than the second threshold, user guidance may not be automatically provided but the user with the proficiency score greater than the second threshold may have the option to turn ON user guidance, and may be able to select the greater or lesser amount of user guidance. Similarly, when lesser amount of user guidance is provided, the user may have the option of increasing the amount of guidance.

While the above example illustrates two threshold for proficiency score to automatically provide three levels of guidance (lesser, greater, and none), in some embodiments, more than two thresholds may be used to provide additional levels of guidance to the user.

At 322, method 300 includes computing one or more of an updated proficiency score of the user for the current pre-set, and saving the one or more of an updated proficiency score of the user to a database. In one example, the updated proficiency score may be a proficiency score calculated as a function of one or more scores corresponding to individual proficiency parameters (e.g., the proficiency score 216, based on the user scores 210 of the example pre-sets 200, 230, and 260 of FIG. 2). In another example, the updated proficiency score may be a score assigned to a specific proficiency parameter (e.g., an updated user score 210 of FIG. 2), or one or more parameter-specific proficiency scores (e.g., user scores 210) and an overall proficiency score (e.g., proficiency score 216) may be updated.

As described above in relation to example pre-sets 200, 230, and 260 of FIG. 2, in one example, the updated proficiency score may be a moving average of a new proficiency score of the user on the examination with one or more historical user proficiency scores from previous ultrasound examinations performed by the user on the same pre-set. In other examples, the updated proficiency score may be determined as a result of a different function of the user's proficiency score on the examination and one or more historical user proficiency scores from previous ultrasound examinations performed by the user on the same pre-set.

The updated proficiency score may be saved to a database such as the proficiency database 132 of ultrasound imaging system 100 of FIG. 1. In an embodiment, the updated proficiency score may overwrite or replace a previous proficiency score, such that a single proficiency score is always stored that represents the current proficiency of the user. In other embodiments, new proficiency scores that are generated may be stored in the database, whereby an updated proficiency score may be calculated dynamically, on demand, based on the user's individual proficiency scores collected over time for each examination performed. In still further embodiments, the new proficiency score and the updated proficiency score may both be recorded in the database. It should be appreciated that the determination and recording of the user's proficiency score(s) is described herein for illustrative purposes, and proficiency scores for the user may be determined and recorded in other ways without departing from the scope of this disclosure.

Once method 300 has computed and saved a proficiency score of the user at 322, method 300 proceeds to 324. At 324, method 300 includes prompting the user whether they wish to end the session. At 326, method 300 includes determining from the user's response whether the user wishes to end the session. If the user wishes to end the session at 326, method 300 proceeds to 328. At 328, method 300 includes saving the current session data, and method 300 ends. Alternatively, if the user does not wish to end the session at 326, method 300 proceeds back to 304, and the user is prompted for a desired pre-set/anatomy of interest to reinitiate scanning, as described above.

Figure 3B:
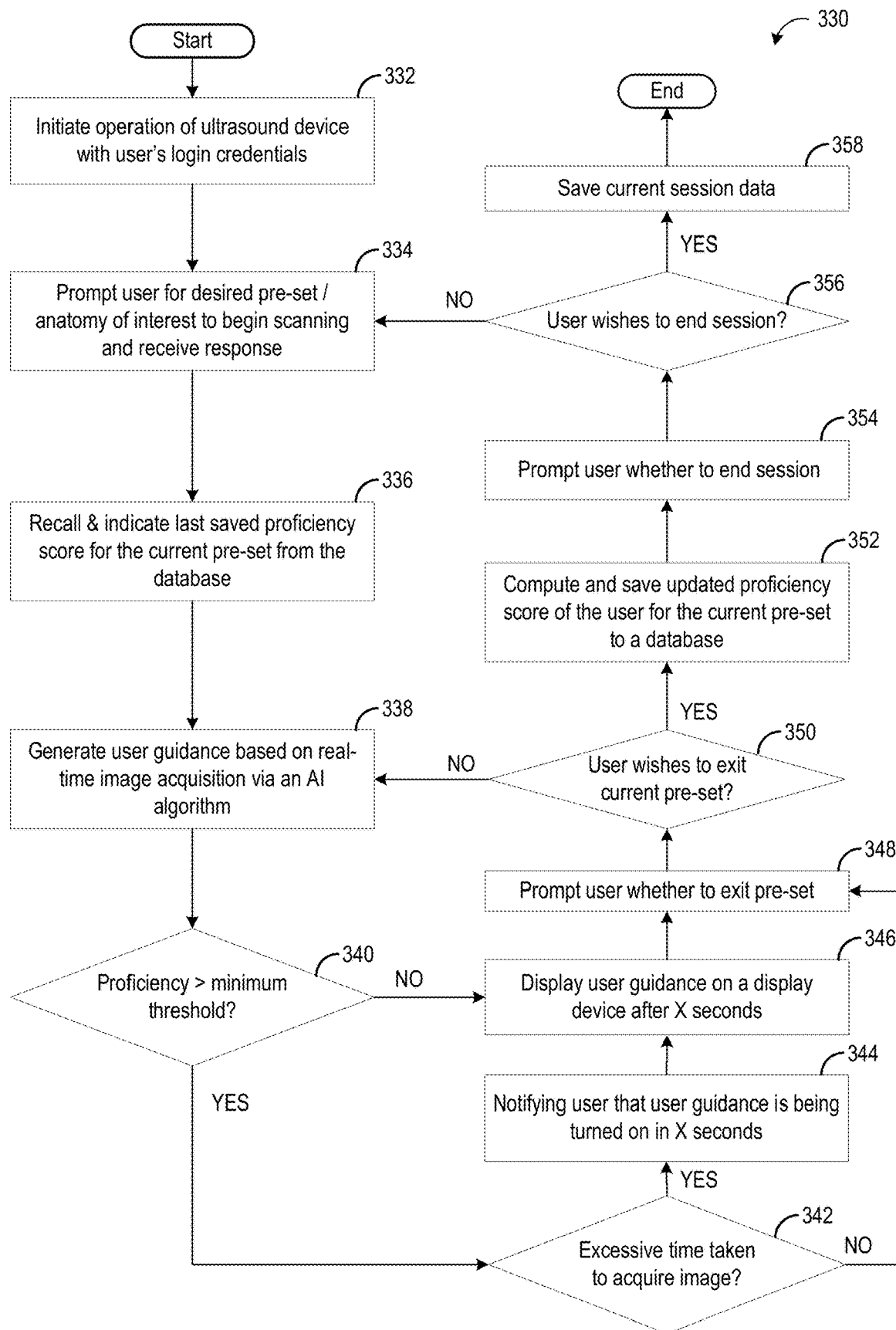
Figure 4A:
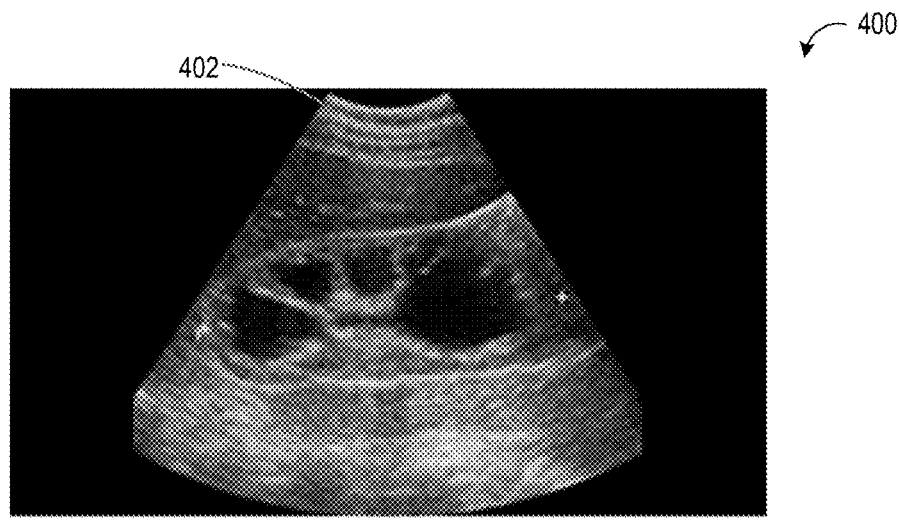
FIGS. 4A, 4B, and 4C are examples of contextual user guidance displays in a user interface for an ultrasound device.
Figure 4B:
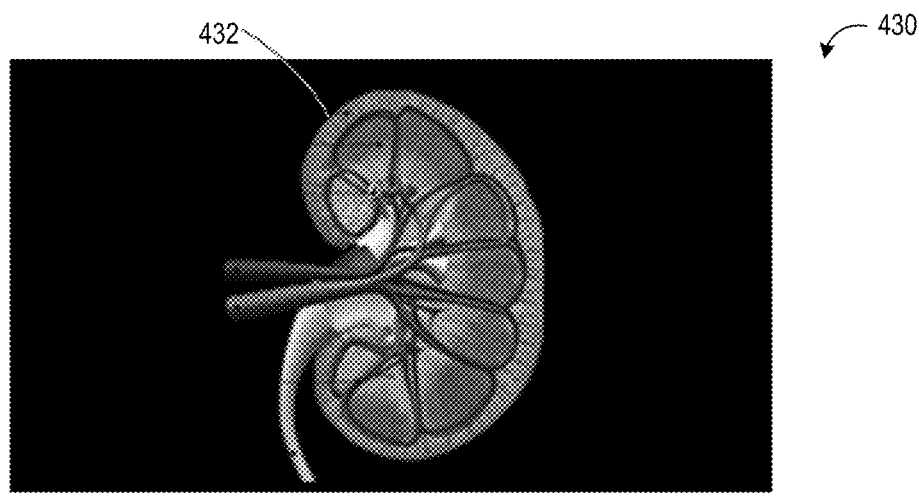
Figure 4C:
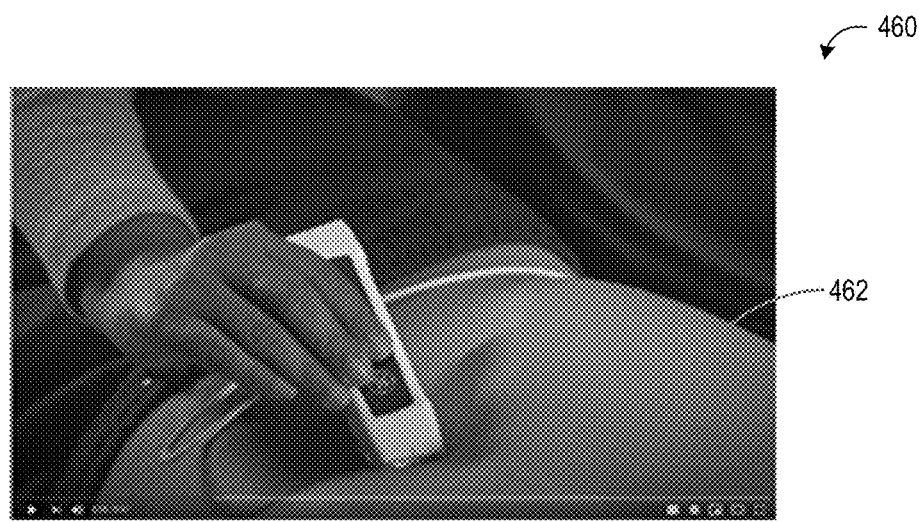

Referring now to FIG. 3B, an example method 330 is shown for automatically generating user guidance, after a duration, to a user on a display device such as the display device 118 of ultrasound system 100 of FIG. 1. For example, during imaging conditions when user guidance (e.g., real-time and/or contextual user guidance) is not initially displayed (e.g., due to the proficiency of the user being greater than the threshold proficiency), method 330 may monitor user's current imaging proficiency via one or more proficiency parameters (e.g., a current speed of acquisition to achieve a desired image having a desired image quality and/or achieving a desired scan plane for the current pre-set), and may automatically activate user guidance when one or more current imaging proficiency conditions (e.g., current acquisition speed is less than a threshold duration taken to acquire desired image, repeatedly not achieving desired scan plane, etc.) are not satisfied. Further, Further, the user may be notified in advance that the user guidance will be displayed to the user. For example, method 330 may further generate a first user guidance prompt indicating that the user is taking excessive duration to acquire a desired image and a duration, which may include a countdown timer, before the user guidance is automatically turned ON.

Method 330 may be carried out by a processor, such as the processor 116 of the ultrasound imaging system 100 of FIG. 1.

In another example, a different proficiency parameter other than acquisition speed may be monitored to determine whether the user is struggling. For example, if a scan plane of an acquired image is not of a desired quality (e.g., if a difference between a scan plane and a target scan plane exceeds a threshold difference), user guidance may automatically be displayed to the user.

Step 332 to 340 of method 330 may be the same as or similar to steps 300 to 310 of method 300. At 332, method 330 includes initiating operation of an ultrasound device with login credentials of the user. At 334, method 330 includes prompting the user for a desired pre-set/anatomy of interest to begin scanning and receiving a response back from the user. At 336, method 330 includes recalling and indicating the last save proficiency score for the current pre-set from the database. At 338, method 330 includes generating user guides based on real-time image acquisition via an AI algorithm. At 340, method 330 includes determining whether a proficiency score of the user exceeds a minimum threshold proficiency score.

At 342, method 330 includes determining whether excessive time is being taken to acquire a suitable image (e.g., of a desired quality). For example, for a liver pre-set, a predetermined threshold duration (e.g., 60 seconds) may be established for acquiring an image of a liver above a threshold quality (for example, as described above in relation to FIGS. 2A-2C) and in a correct scan plane. If an amount of time taken by the user exceeds the predetermined threshold duration, it may be determined (e.g., by the processor) that excessive time is being taken to acquire an image. Alternatively, if the amount of time taken by the user does not exceed the predetermined threshold duration, it may be determined that excessive time is not being taken to acquire an image.

If method 330 determines at 342 that excessive time is not being taken to acquire a suitable image, method 330 proceeds to 344. At 344, method 330 includes prompting the user whether to exit the pre-set (e.g., at the completion of the examination). Alternatively, if method 330 determines at 342 that excessive time is being taken to acquire a suitable image, method 330 proceeds to 344. At 344, method 330 includes notifying the user that guidance is being turned on after the duration has elapsed.

For example, an ultrasound operator with an intermediate level of experience and a proficiency score of 5.0, out of a maximum proficiency score of 10.0, may be performing a current ultrasound examination via an ultrasound imaging system such as ultrasound imaging system 100 of FIG. 1. The operator's proficiency score of 5.0 may be above a pre-established minimum threshold proficiency score of 4.0 at 354, meaning that user guidance is not displayed by default on the display device. However, in the current ultrasound examination the operator may have more difficulty acquiring a suitable image than usual (e.g., because of a patient's body type, age, the operator's degree of fatigue, etc.). A processor of the ultrasound imaging system (e.g., the processor 116 of FIG. 1) may determine that the amount of time being taken to acquire a suitable image (e.g., several minutes) exceeds a threshold reference duration for acquiring a suitable image (e.g., one minute), and as a result may notify the user that guidance will be turned on after a predetermined time period has elapsed (e.g., 60 seconds). The threshold reference duration may be established based on an amount of time allocated for a patient examination, an expected duration based on the user's proficiency level, an amount of time taken to acquire a suitable image by an expert operator, the type of ultrasound examination, a historical evolution of the user's proficiency over time, and/or any other relevant factors or combination of factors. The predetermined time period may be established based on historical data and/or offline studies. In other examples, a different proficiency parameter other than speed may be monitored.

After the user is notified that guidance will be turned on at 344, method 330 proceeds to 346. At 346, method 330 includes displaying the user guidance on the display device after the predetermined time period has elapsed (e.g., 10 seconds). An example notification that user guidance will be turned on is shown in FIG. 6C and described in greater detail below. Briefly, the first prompt or the notification that the user guidance will be turned ON may be provided as a transparent or translucent overlay on a portion of the real-time acquired image.

Steps 348 to 358 of method 330 may be the same as or similar to steps 318 to 328 of method 300. At 348, method 330 includes prompting the user whether to exit the pre-set. At 350, method 330 includes determining whether the user wishes to exit the current pre-set. If the user does not wish to exit the current pre-set at 350, method 330 proceeds back to 338, and guidance continues to be generated based on real-time image acquisition via an AI algorithm. If the user does wish to exit the current pre-set at 350, method 330 proceeds to 352. At 352, method 330 includes computing and saving an updated proficiency score of the user for the current pre-set to a database. At 354, method 330 includes prompting the user whether to end the session. At 356, method 330 includes determining whether the user wishes to end the session based on a response from the user at 354. If the user does not wish to and the session at 356, method 330 includes proceeding back to 334, and the user is prompted for a new desired pre-set to begin scanning. Alternatively, if the user wishes to end the session at 356, method 330 proceeds to 358. At 358, method 330 includes saving the current session data, and method 330 ends.

In some embodiments, when less than maximum user guidance is being provided to the user (e.g., when the proficiency score of the user is greater than a first lower threshold but less than a second higher threshold, a lesser amount of user guidance may be provided to the user), a greater amount (e.g., lesser amount of guidance increased to maximum user guidance) of user guidance is automatically provided to the user when the user takes an excessive amount of time to acquire the desired image. As an example, the lesser amount of user guidance may be real-time user guidance or contextual user guidance, while greater amount of user guidance may include both real-time and contextual user guidance. In some examples, lesser amount of user guidance may include lesser amount of real-time guidance and/or lesser amount of contextual guidance while greater amount of user guidance may include greater amount of real-time guidance and/or greater amount of contextual guidance. In a non-limiting example, the lesser amount of real-time guidance may include one or more but not all of probe-pose adjustment graphical cues, textual instructions indicating current/subsequent steps to be performed, and automatic AI based acquisition of images, while greater amount of real-time guidance may be based on the lesser amount of real-time guidance and may include all of the real-time guidance types indicated above. Similarly lesser amount of contextual guidance may not include all of the contextual guidance types including pre-acquire image showing desired scan plane, graphical illustration (e.g., text book illustration) of the related anatomy, and educational video for the related exam, while the greater amount of contextual guidance may be based on the lesser amount of contextual guidance and may include all of the contextual guidance types indicated above.

In some examples, the first prompt may include an indication that the user guidance will be automatically increased. Further, the first prompt may additionally or alternatively include an indication of the type of guidance that may be additionally provided. That is, the first prompt may indicate whether real-time guidance is increased or contextual guidance is increased or both are increased. Furthermore, in some examples, the first prompt may specify which type of real-time guidance (e.g., probe-pose adjustment graphical cues, textual instructions indicating current/subsequent steps to be performed, and automatic AI based acquisition of images) and/or which type of contextual guidance (e.g., pre-acquired image, graphical illustration (e.g., text book illustration) of the related anatomy, and educational video for the related exam) will be automatically applied.

Figure 3C:
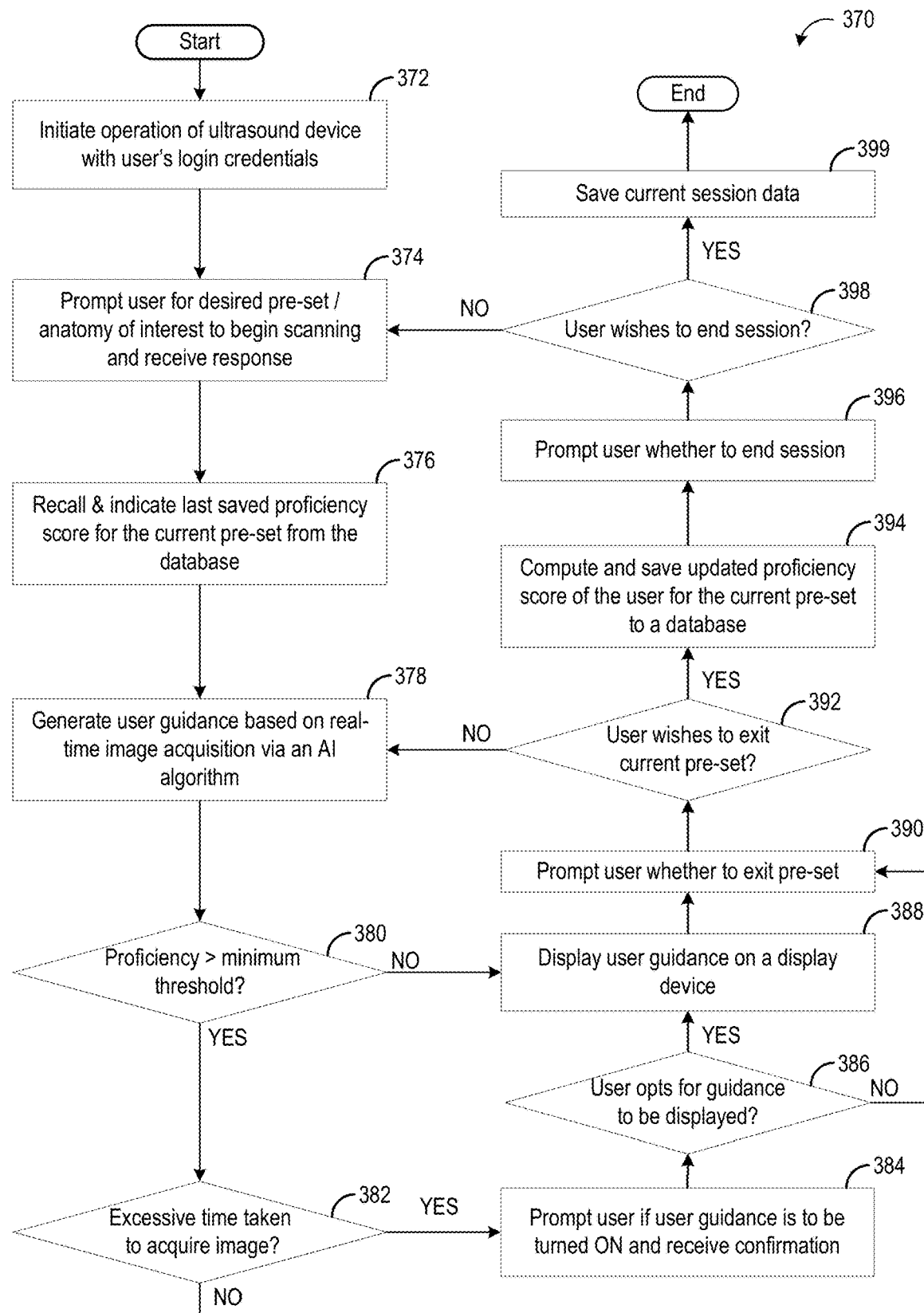

Referring now to FIG. 3C, an example method 370 is shown for displaying an option for activating user guidance to a user on a display device, such as the display device 118 of ultrasound system 100 of FIG. 1, during imaging conditions when excessive time is being taken to acquire an ultrasound image. For example, when a proficiency score for the user performing the imaging is greater than a threshold proficiency, the user guidance may not be initially displayed. However, during certain imaging conditions, such as when a duration to obtain a desired quality image is greater than a threshold duration (e.g., threshold duration based on a proficiency level, such as proficiency level 208 at FIG. 2), an option to activate user guidance and/or provide additional user guidance may be provided as discussed below.

One indication that the user may be struggling may be that a time taken to acquire an image may exceed a predetermined threshold duration. Method 370 may be carried out by a processor, such as the processor 116 of the ultrasound imaging system 100 of FIG. 1, in accordance with instructions stored in non-transitory memory of a computing device, such as memory 120 of ultrasound imaging system 100 of FIG. 1.

As described above in relation to FIG. 3B, a different proficiency parameter other than acquisition speed may be monitored to determine whether the user is struggling. For example, if it is determined that a user is unable to achieve a target scan plane repeatedly on the same patient, the user may be prompted whether user guidance should be displayed to the user.

Step 372 to 382 of method 370 may be the same as or similar to steps 300 to 310 of method 300. Briefly, at 372, method 370 includes initiating operation of an ultrasound device with login credentials of the user. At 374, method 370 includes prompting the user for a desired pre-set/anatomy of interest to begin scanning and receiving a response back from the user. At 376, method 370 includes recalling and indicating the last save proficiency score for the current pre-set from the database. At 378, method 370 includes generating user guides based on real-time image acquisition via an AI algorithm. At 380, method 370 includes determining whether a proficiency score of the user exceeds a minimum threshold proficiency score. If it is determined at 380 that the proficiency score of the user is below the threshold proficiency score, method 370 proceeds to 388. At 388, method 370 includes displaying the user guidance on the display device. As discussed above, the user guidance may include real-time user guidance and/or contextual user guidance. Alternatively, if it is determined at 380 that the proficiency score of the user exceeds the threshold proficiency score, method 370 proceeds to 382. At 382, method 370 includes determining whether excessive time is being taken to acquire the image.

If it is determined at 382 that excessive time is not being taken to acquire an image (e.g., as described above in relation to FIG. 3B), method 370 proceeds to 390. At 390, the user is prompted whether to exit the pre-set, as described above in relation to methods 300 and 330 of FIGS. 3A and 3B. Alternatively, if it is determined at 382 that excessive time is being taken to acquire a desired image, method 370 proceeds to 384. Parameters for determining whether excessive time is taken to acquire the desired image is discussed at FIG. 3B, and will not be repeated for the sake of brevity. At 384, method 370 includes prompting the user whether to turn ON the user guidance, and receiving a response from the user. For example a prompt may be displayed on the display portion of the graphical user interface. The prompt may include one or more indications including an indication that the user taking excessive time to acquire the desired image and/or scan plane and requesting confirmation to turn ON user guidance. Further, the one or more indications may include a first control button to confirm turning ON user guidance and a second control button to cancel the prompt and/or user guidance. Furthermore, the one or more indication include one or more graphical indications, such as a timer, clock, etc. Example prompt for turning ON user guidance is further described with respect to FIG. 6D. Further still, as shown in FIG. 6D, the prompt may be displayed as a translucent or transparent overlay on a portion of the acquired ultrasound image.

In some embodiments, while it may be determined that a novice operator may benefit from an automatic display of user guidance, and that an expert operator may not benefit from a display of user guidance, an intermediate proficiency range may exist where it is not clear whether a user would benefit from the display of user guidance or not. In such cases, when it is determined that the user may be struggling (e.g., duration to acquire the desired image is greater than the threshold duration), it may be desirable to provide the user with an option to display user guidance (if the user guidance is turned OFF initially due to proficiency being greater than a second higher threshold) or provide additional user guidance (if maximum user guidance is not displayed due to proficiency being greater than a first minimum threshold but less than the second higher threshold). Accordingly, in some embodiments, the prompts may include control buttons to increase user guidance or cancel future increase in user guidance.

Next, upon prompting the user, method 370 proceeds to 386. At 386, method 370 determines whether the user has opted for guidance to be displayed. If it is determined at 386 that the user has not opted for guidance to be displayed, method 370 proceeds to 390. At 390, method 370 includes prompting the user whether to exit the pre-set, as described above in relation to FIGS. 3A and 3B. Alternatively, if it is determined at 386 that the user has opted for guidance to be displayed, method 370 proceeds to 388. At 388, method 370 includes displaying user guidance on the display device. In this way, a user who is having difficulty acquiring a suitable image may be provided the option of receiving guidance upon request.

As a non-limiting example, an ultrasound operator with an intermediate level of experience and a proficiency score of 5.0, out of a maximum proficiency score of 10.0, may be performing a current ultrasound examination via an ultrasound imaging system such as ultrasound imaging system 100 of FIG. 1. The operator's proficiency score of 5.0 may be above a pre-established minimum threshold proficiency score of 4.0 at 380, meaning that user guidance is not displayed by default on the display device. However, in the current ultrasound examination the operator may have more difficulty acquiring a suitable image than usual (e.g., because of a patient's body type, age, the operator's degree of fatigue, etc.). A processor of the ultrasound imaging system (e.g., the processor 116 of FIG. 1) may determine that the amount of time being taken to acquire a suitable image (e.g., several minutes) exceeds a threshold reference duration for acquiring a suitable image (e.g., one minute), and as a result may ask the user whether the user wishes to receive guidance in acquiring a suitable image. As described above, the threshold reference duration may be established based on the user's previous performance on similar examinations, an amount of time allocated for a patient examination, an expected duration based on the user's proficiency level, an amount of time taken to acquire a suitable image by an expert operator, and/or any other relevant factors or combination of factors.

Steps 390 to 399 of method 370 may be the same as or similar to steps 318 to 328 of method 300. At 390, method 370 includes prompting the user whether to exit the pre-set. At 392, method 370 includes determining whether the user wishes to exit the current pre-set. If the user does not wish to exit the current pre-set at 392, method 370 proceeds back to 378, and guidance continues to be generated based on real-time image acquisition via an AI algorithm. If the user does wish to exit the current pre-set at 392, method 370 proceeds to 394. At 394, method 370 includes computing and saving an updated proficiency score of the user for the current pre-set to a database. At 396, method 370 includes prompting the user whether to end the session. At 398, method 370 includes determining whether the user wishes to end the session based on a response from the user at 396. If the user does not wish to end the session at 398, method 370 includes proceeding back to 374, and the user is prompted for a new desired pre-set to begin scanning. Alternatively, if the user wishes to end the session at 398, method 370 proceeds to 399. At 399, method 370 includes saving the current session data, and method 370 ends.

In this way, methods 300, 330, and 370 illustrate how contextual information and real-time guidance cues may be alternatively enabled or disabled, with or without notification to the user, and timed in order to provide customized guidance to an ultrasound operator based on their proficiency and/or a difficulty with which they are attempting to acquire ultrasound images. A process for progressively assessing the operator's proficiency and updating the operator's proficiency score is provided, such that the user guidance may be provided in a way that is helpful to operators at lower experience levels, yet not a distraction to operators with higher experience levels.

Further, in some embodiments, the methods 300, 330, and/or 370 may be adjusted, and/or steps of the methods 300, 330, and/or 370 may be combined to generate methods for training purposes. In one example, automated training may be provided to a user whereby the user is instructed to follow a series of procedural steps. The proficiency score of the user may be used to determine what procedural steps to include, and/or how the procedural steps might be displayed, and/or how long the procedural steps may be displayed on a screen of the display device. In another example, one or more types of user guidance may be displayed as part of a predetermined sequence to be followed by the user, where the timing and/or other characteristics of the sequence may be adjusted based on the proficiency score of the user. For example, a novice user with a low proficiency score may be presented with a set of instructions to follow, and provided a first duration to complete the instructions, while an intermediate user with a higher proficiency score may be presented with a set of instructions to follow, and provided a second, longer duration to complete the instructions.

Figure 5A:
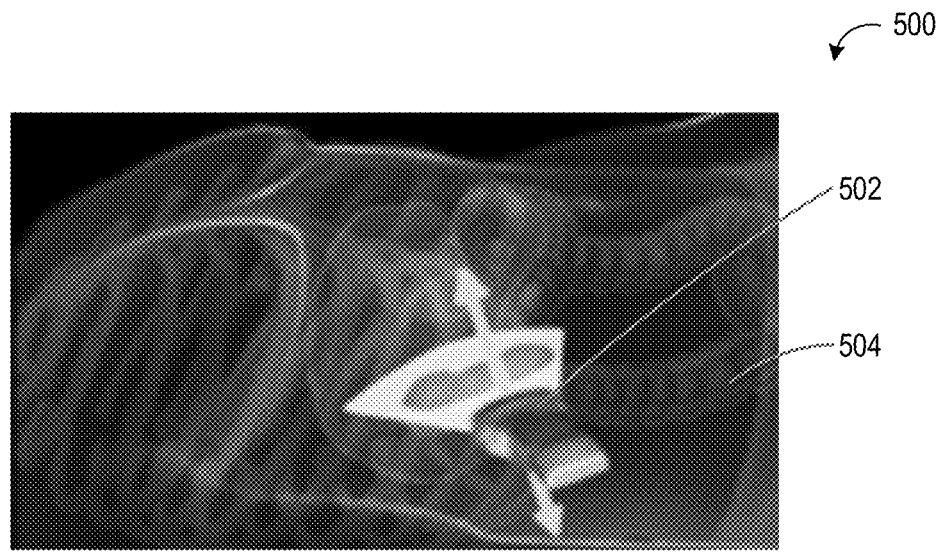
FIGS. 5A and 5B are examples of real-time user guidance displays in a user interface for an ultrasound device.
Figure 5B:
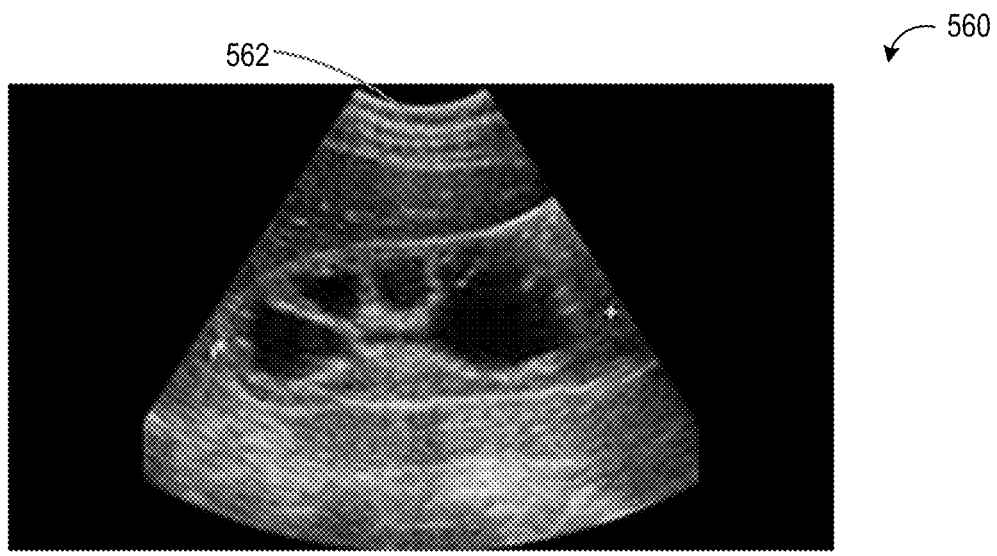

As described above, user guidance may include contextual user guidance and/or real-time user guidance. Contextual user guidance includes reference elements such as images, videos, etc. that provide the user with reference information that is not time dependent, and that may be consulted to aid the user in acquiring ultrasound images. In contrast, real-time user guidance includes time-dependent visual elements such as probe adjustment cues, textual instructions, prompts, checklists, AI triggered automated images acquired in a live session, and/or other visual elements that provide aid to a user at a specific moment in time based on the real-time display of ultrasound images. FIGS. 4A, 4B, and 4C show examples of contextual user guidance, while FIGS. 5A and 5B show examples of real-time user guidance.

Referring now to FIGS. 4A, 4B, and 4C, example contextual guidance displays are shown that may be displayed to a user on a display device of an ultrasound imaging system such as the ultrasound imaging system 100 of FIG. 1. As described in more detail below in relation to FIGS. 6A-6D, the example contextual guidance displays may be displayed concurrently with ultrasound images acquired in real time via an ultrasound probe (e.g., the ultrasound probe 106 of ultrasound system 100 of FIG. 1), such that the user may consult the example contextual guidance displays while adjusting the ultrasound probe to acquire a suitable image. As described above in relation to FIGS. 3A and 3B, the contextual guidance displays may be generated automatically by an AI algorithm running in a processor of the ultrasound imaging system (e.g., the processor 116 of the ultrasound system 100 of FIG. 1).

FIG. 4A shows an example contextual reference guidance display 400. The contextual guidance display 400 may include a pre-acquired reference ultrasound image 402, which may be acquired from a prior patient examination. For example, the reference ultrasound image 402 may be a target image of an anatomical feature that the user is attending to acquire, which the user may compare to an image generated in real time as result of adjusting a position and/or orientation of an ultrasound probe (e.g., the ultrasound probe 106 of the ultrasound imaging system 100 of FIG. 1).

FIG. 4B shows an example contextual guidance display 430, which may include a reference anatomical illustration 432. For example, the reference anatomical illustration 432 may include a graphical illustration of an anatomical feature of which the user is attempting to acquire ultrasound images, taken from an external source such as a textbook, online reference materials, 3-D model, etc. The reference anatomical illustration may include a full representation of the target anatomical feature, or the reference anatomical illustration 432 may include a portion of the target anatomical feature (e.g., a relevant section or cross-section, a partial view, etc.). The reference anatomical illustration 432 may be used by the user to identify and/or locate one or more anatomical structures of the target anatomical feature. For example, a user attempting to acquire ultrasound images of a spleen may be displayed a graphical illustration of a spleen with component anatomical structures identified via labels, to aid the user in orienting the ultrasound probe.

FIG. 4C shows an example contextual guidance display 460, which may include a video feed 462 that provides guidance to the user. In an embodiment, the video feed 462 may be a training or educational video that provides instructions regarding how an ultrasound device may be adjusted relative to a body of a patient in order to acquire ultrasound images. In another embodiment, the video feed 462 may be a live video feed from another operator (e.g., a more experienced operator, a trainer, etc.) that provides customized instruction and/or other information relevant to acquiring ultrasound images. In some examples, the video feed 462 may include audio, which the user may receive via a peripheral device (e.g., speakers, headphones, etc.), or the video feed 462 may include other forms of presenting information, such as slideshows, animations, multimedia presentations, etc.

Referring now to FIGS. 5A and 5B, example real-time guidance displays are shown that may be displayed to a user on a display device of an ultrasound imaging system such as the ultrasound imaging system 100 of FIG. 1. As described in more detail below in relation to FIGS. 6A-6D, the example real-time reference guidance displays may be displayed concurrently with ultrasound images acquired in real time via an ultrasound probe (e.g., the ultrasound probe 106 of ultrasound system 100 of FIG. 1), such that the user may receive aid in the form of textual or visual instructions that relate to the specific ultrasound images acquired as the user adjusts a position, and/or orientation the ultrasound probe to acquire a suitable image. As described above in relation to FIGS. 3A, 3B, and 3C, the real-time guidance displays may be generated automatically by an AI algorithm running in a processor of the ultrasound imaging system (e.g., the processor 116 of the ultrasound system 100 of FIG. 1).

Referring now to FIG. 5A, an example real-time visual guidance display 500 of a user interface of an ultrasound device is shown. The real-time visual guidance display 500 may include a guidance cue 502, which may indicate to a user a suggested adjustment to the ultrasound device in order to more accurately acquire an ultrasound image. For example, the guidance cue 502 may include a visual representation of an ultrasound device with a visual indication of a direction to move the ultrasound device in, an adjustment to be made to the pressure applied to the ultrasound device, etc. In an embodiment, the guidance cue 502 may be superimposed on a contextual guidance display that includes a reference image. As one example, the guidance cue 502 may be superimposed on as a view of a 3-D rendering of a target anatomical feature. Alternatively, the guidance cue 502 may be superimposed on a graphical illustration of a target anatomical feature (e.g., the contextual guidance display 432 of contextual reference guidance display 430 of FIG. 4), or a reference ultrasound image (e.g., the contextual guidance display 402 of contextual reference guidance display 400 of FIG. 4), or any other type of image relevant to the acquisition of ultrasound images.

FIG. 5B shows an example real-time reference guidance display 560, which may include an ultrasound image 562 that may be automatically acquired by an AI algorithm running in a processor of the ultrasound imaging system and displayed for reference purposes to the user. In an embodiment, the ultrasound image 562 may be an image of a target anatomical feature that the user is attempting to acquire, which the user may compare to an image generated in real time as result of adjusting a position and/or orientation of the ultrasound device. For example, a user attempting to achieve a target scan plane for acquiring a suitable ultrasound image of a spleen may acquire ultrasound images that oscillate between the target scan plane and one or more adjacent scan planes, and may encounter difficulty distinguishing the target scan plane from the one or more adjacent scan planes. To aid the user, an AI algorithm running in the processor of the ultrasound imaging system may identify the ultrasound image corresponding to the target scan plane, and display the ultrasound image to the user as a guide.

In other embodiments, other types of real-time guidance may be provided. As one example, textual guidance may be provided in terms of written instructions that are displayed on a screen of the display device. In one embodiment, the textual guidance may be displayed on a small and/or unused portion of the screen of the display. In another embodiment, the textual guidance may be superimposed on other elements of the user guidance. For example, textual guidance may be superimposed on the ultrasound image 562. In one example, textual guidance may be superimposed on the ultrasound image 562 to label one or more anatomical structures. In another example, a plurality of steps of a procedure may be displayed as a reference to the user.

Referring now to FIGS. 6A, 6B, 6C, and 6D, example user interface views 600, 620, 640, and 660 of an ultrasound imaging system display device are shown. The ultrasound display device may be the same as or similar to the display device 118 of ultrasound imaging system 100 of FIG. 1. In user interface views 600, 620, 640, and 660, a display device 602 is shown in the form of a smart phone, which is communicatively coupled to an ultrasound probe such that images acquired by the ultrasound probe are displayed on the display device 602. In other embodiments, the display device 602 may be in the form of a computer tablet, a computer monitor, a computer screen of an ultrasound imaging system, a screen of a handheld ultrasound imaging device, or any other type of display screen on which ultrasound images may be displayed.

The display device 602 includes a display screen portion 604 on which visual display elements may be displayed in real-time, including ultrasound images being acquired, reference images, guidance cues, text, graphical display elements, etc. As described herein, the visual display elements may be generated upon request by a user and/or generated automatically based on an AI algorithm.

Some of the visual display elements may be unrelated to a proficiency score of the user. In one example, a first indicator field 607 may be displayed on the screen 604. The first indicator field 607 may include elements that are unrelated to the proficiency score of the user. The first indicator field 607 may include a power level indicator 605 and/or a pre-set indicator 606. The pre-set indicator 606 may indicate the pre-set in which images are being acquired. In an embodiment, the pre-set indicator 606 may be a graphical display element such as an icon depicting a target anatomical feature. For example, for a liver pre-set, the pre-set indicator 606 may be an icon depicting a liver. In other embodiments, the pre-set indicator may be an identifier (e.g., a letter, a code, a number, etc.), or the pre-set indicator may be another type of symbol that indicates to the user the current pre-set loaded onto the display device 602. The screen 604 may further include display of a second indicator field 611. The second indicator field 611 may also include elements that are unrelated to the proficiency score of the user. The second indicator field 611 may include an identifying label 610 that may be used to identify an examination being performed and/or an operator. For example, the identifying label 610 may include an ID number of the exam, an ID number of the operator, an image of the operator's face, the name of the operator, or any other information that may be used to identify the examination or the operator. In some examples, the second indicator field 611 may include an icon that corresponds to the user or the exam or the pre-set.

Other visual display elements may include information relating to the proficiency score of the user, or may be displayed as a result of the proficiency score of the user. In particular, the screen 604 may include a proficiency indicator 608 that indicates the user's proficiency on the current pre-set. In some examples, the proficiency indicator 608 may be a proficiency score of the user, where the proficiency score of the user is calculated as described above in relation to FIG. 2. In other examples, the proficiency indicator may be a representation of a proficiency score of the user (e.g., expressed as a percentage of a total proficiency, or as a pie/bar chart, etc.), and/or a representation of a proficiency level of the user, where the proficiency level of the user is determined by a mapping function applied to the proficiency score of the user.

In an embodiment, the proficiency indicator 608 may use colors to indicate a proficiency level of the operator, whereby a color may indicate that the user has achieved a proficiency score on a loaded pre-set above a threshold proficiency value associated with the color (e.g., green if the user's proficiency score is above a first threshold proficiency value, blue if the user's proficiency score is above a second threshold proficiency value, red if the user's proficiency score is above a third threshold proficiency value, etc.). For example, the proficiency indicator 608 may be an orange bar to indicate that the user's proficiency score is above a first threshold corresponding to a novice ultrasound operator, while the proficiency indicator 608 may be a green bar to indicate that the user's proficiency score is above a second threshold corresponding to an ultrasound operator of an intermediate level. It should be appreciated that the examples included herein are for illustrative purposes and the proficiency indicator 608 may use another type of display element to indicate a proficiency score and/or proficiency level of the user without departing from the scope of this disclosure.

The screen 604 may include an image display area 612, in which ultrasound images acquired via an ultrasound probe (e.g., the ultrasound probe 106 of ultrasound system 100 of FIG. 1) may be displayed. In an embodiment, the ultrasound images are displayed in real time as the user adjusts a position, and orientation, and/or a pressure of the ultrasound probe on a body of a patient. For example, during an ultrasound examination of a uterus, ultrasound images of the uterus acquired via the ultrasound probe may be displayed in the display area 612 of the display device 602. As the user adjusts the ultrasound probe, the ultrasound images displayed in the display area 612 may shift to reflect a new position, orientation, or pressure of the ultrasound probe. For example, if the user adjusts the orientation of the ultrasound probe, the ultrasound images displayed in the display area 612 may rotate in accordance with the adjustment made by the user. Similarly, if the user adjusts the position of the ultrasound probe in a direction to a new position, the image is displayed in the display area 612 may be adjusted horizontally in the same or an opposite direction.

Further, the display screen 604 may include display of one or more additional elements 613, 615, and 617 within a third indicator field 609 that may relate to a current operation of the ultrasound probe. The additional elements 613, 615, and 617 may be icons that indicate a current scan mode, or may represent controls for enabling the user to perform one or more operations, such as freeze screen or capture image, for example. These additional elements 613, 615, and 617 may not be related to the proficiency score of the user, and may be displayed on the screen 604 in addition to elements in the first and second indicator fields 607 and 611, which are also not related to the proficiency score of the user.

Taken together, the display screen portion 604 may include display of visual elements that are related to a current proficiency score of the user (e.g., proficiency indicator 608) while also including display of one or more visual elements that are unrelated to the proficiency score (e.g., first, second, and third indicator fields 607, 611, and 609, and visual display elements therein).

Figure 6A:
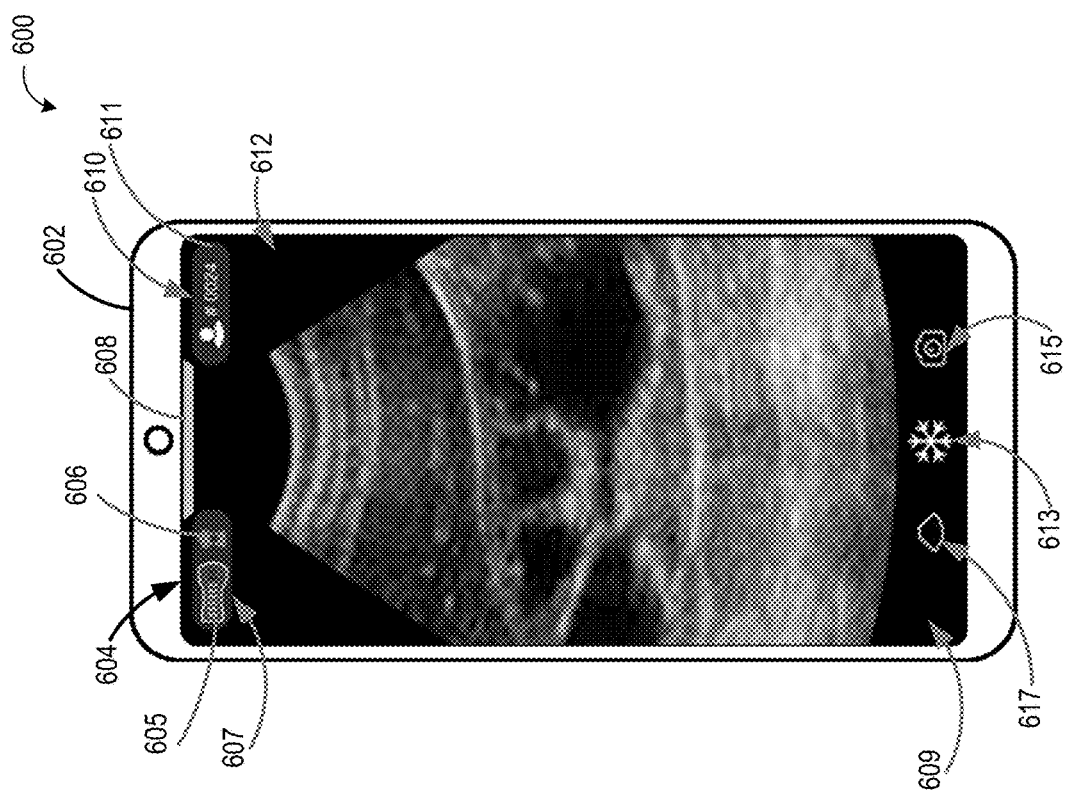
Figure 7A:
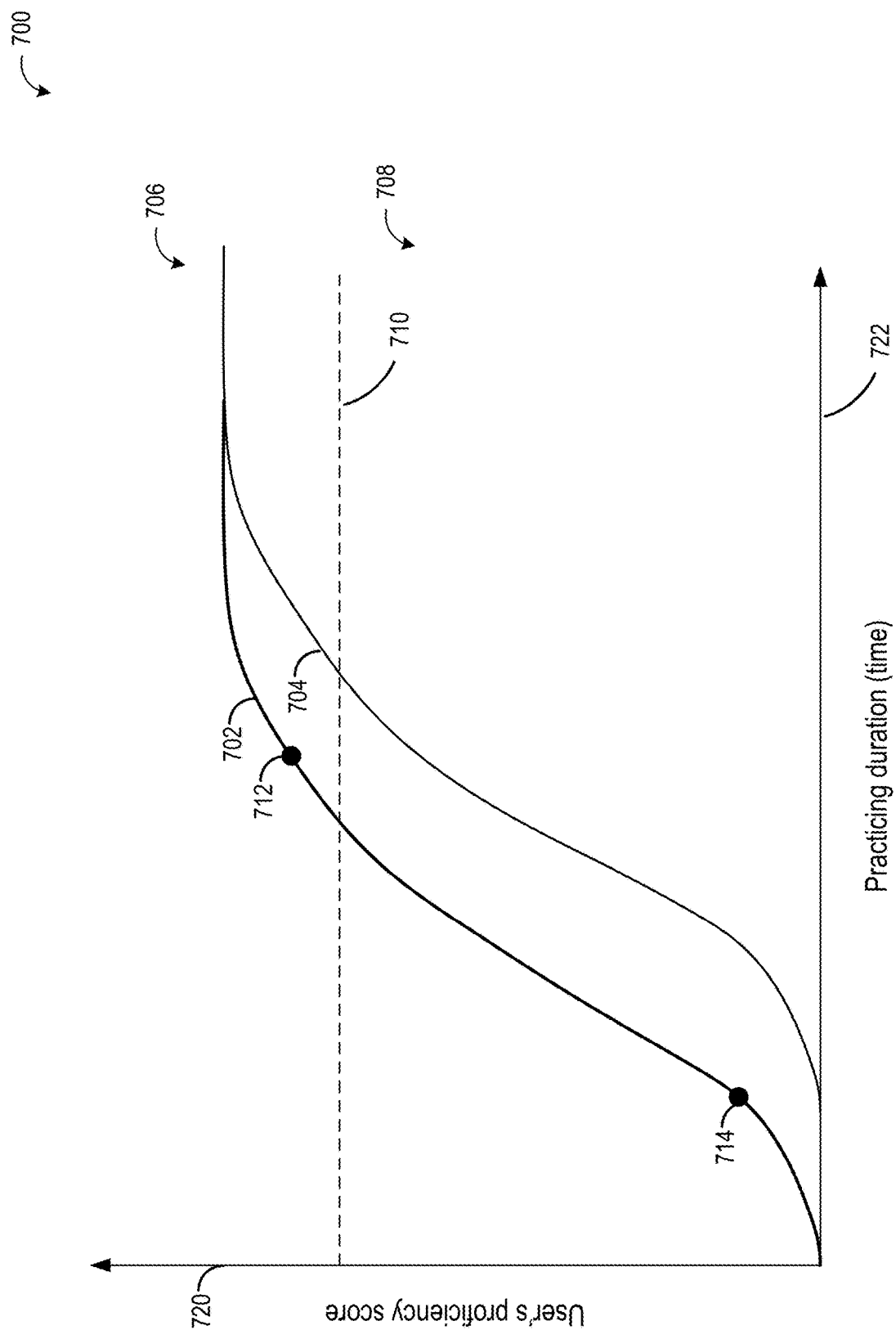
FIG. 7A is a plot showing change in user proficiency on an ultrasound device over a practicing duration and including a common threshold for more than one anatomical region.
Figure 7B:
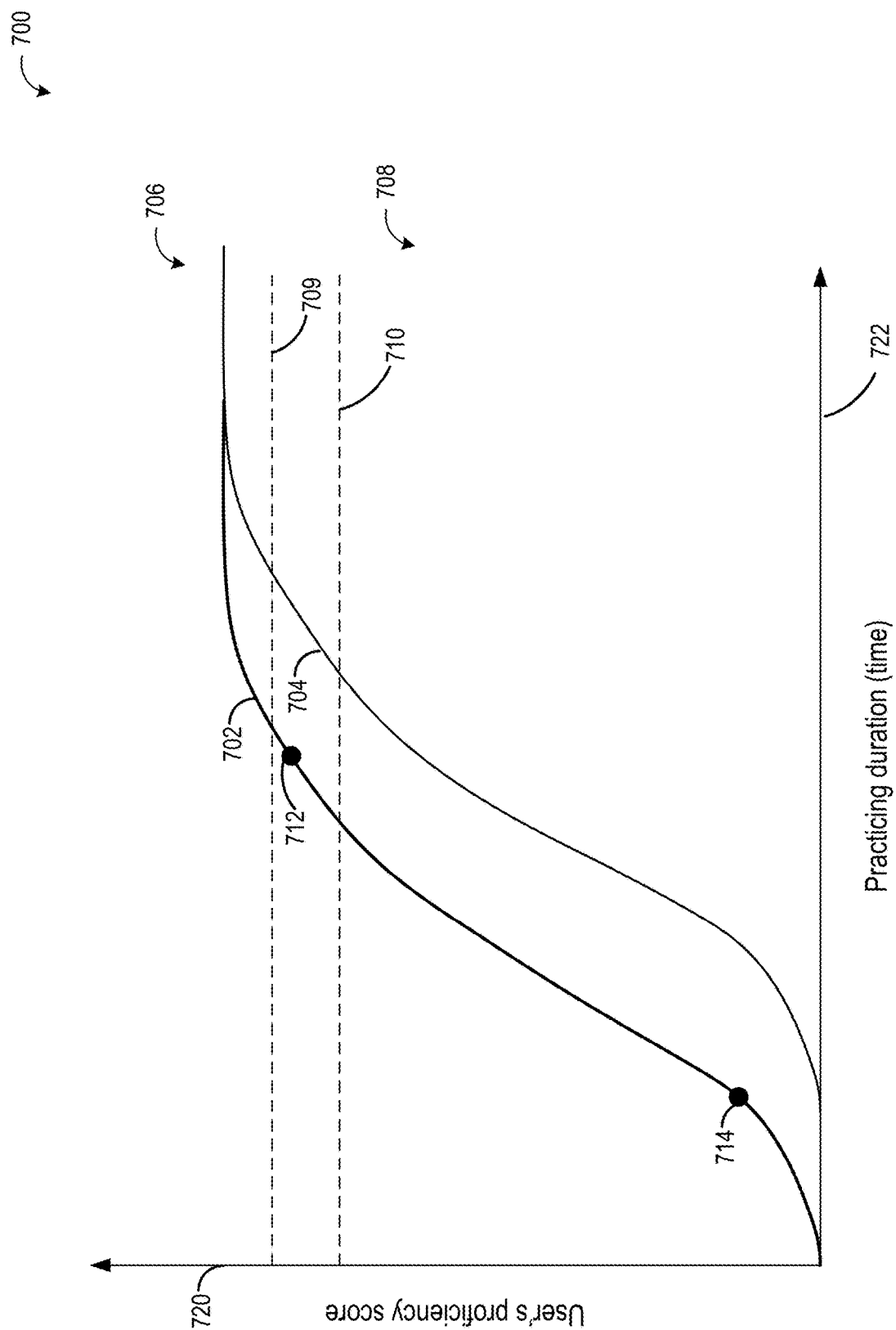
FIG. 7B is a plot showing a change in user proficiency on an ultrasound device over a practicing duration and including different thresholds for different anatomical regions.

Thus, FIG. 6A shows an example configuration of the display device 602 in which user guidance is turned OFF and no user guidance cues or reference images are displayed to the user. Referring now to FIG. 6B, user interface view 620 shows an example configuration of the display device 602 in which user guidance is turned ON. A guidance display 614 is displayed on the screen 604, on top of and partially obscuring the display area 612 where the ultrasound images being acquired via the ultrasound probe are displayed. For example, the guidance display 614 may be displayed as a partially transparent or translucent overlay over a portion of the ultrasound image. As depicted in FIG. 6B, the guidance display 614 may include one or more contextual guidance reference images. For example, the guidance display 614 may include a reference anatomical image 616 of the target anatomical feature (e.g., a liver, spleen, lung, etc.) being scanned, to aid the operator in identifying anatomical structures of the target anatomical feature. In an embodiment, the reference anatomical image 616 may be a view of a 3-D rendering of the target anatomical feature. In another embodiment, the reference anatomical image 616 may be a reference ultrasound image acquired previously by the operator or by another operator from the same patient or from a different patient (e.g., the reference ultrasound image 402 of contextual reference guidance display 400 of FIG. 4A), or the reference anatomical image 616 may be an image from another source, or any other type of image that may be used to aid the operator and identifying anatomical structures of the target anatomical feature.

The guidance display 614 may include one or more real-time visual guidance cues 618. In the embodiment depicted in FIG. 6B, a visual guidance cue 618 in the form of an image of an ultrasound probe is superimposed upon a reference image displayed in the guidance display 614, where a field of view of the probe is indicated along with two arrows indicating a ground plane in reference to which the position of the ultrasound probe may be adjusted. Thus, the visual guidance cue 618 depicted in FIG. 6B may aid the operator by indicating a suggested direction in which the position of the ultrasound probe may be adjusted, for example, to achieve a target scan plane, or to bring a target anatomical feature into view, in real-time, while ultrasound images are being acquired and displayed in the display area 612.

In other embodiments, the guidance display 614 may not be displayed (e.g., as depicted in FIG. 6A), and the visual guidance cue 618 may be superimposed on the ultrasound images displayed in the display area 612 (not depicted in FIGS. 6A-6D). For example, the visual guidance cue 618 may be a label with an arrow indicating a specific anatomical feature, where the arrow points to the relevant anatomical feature in the ultrasound images displayed in the display area 612.

In still other embodiments, a plurality of visual display elements may be displayed collectively on a transparent or partially transparent guidance display 614. Referring to FIG. 6C, user interface view 640 shows a configuration of the display device 602 in which a guidance display 614 is displayed on the screen 604, where the guidance display 614 includes a plurality of textual and visual elements positioned on a partially transparent background. Particularly, FIG. 6C shows the guidance display portion 614 displaying one or more indications based on a current performance of the user during the current imaging session. In an embodiment, the guidance display 614 includes a warning label 642, with text that indicates that the user is taking too long to acquire a suitable ultrasound image. User interface view 640 also includes a timer symbol 644, in the form of an icon representing a clock, and a corresponding timer notification 646, which indicate to the user that user guidance (e.g., guidance cues, reference images, etc.) will appear within a duration. For example, as described above in relation to FIGS. 3A and 3B, if it is determined that the amount of time the user is spending in attempting to acquire a suitable ultrasound image exceeds a threshold duration, the user may be notified that user guidance will be displayed within a second duration to aid the user in acquiring a suitable ultrasound image. The second duration may be pre-established, or the duration may be adjusted based on the user's proficiency score, or other factors.

In FIG. 6D, user interface view 660 shows a configuration of the display device 602 in which a guidance display 614 is displayed on the screen 604, where the guidance display 614 of user interface view 640 of FIG. 6C additionally includes a confirmation instruction 662 that prompts the user to confirm whether to turn on user guidance. In user interface view 660, the timer notification 646 of user interface view 640 of FIG. 6C is replaced by a confirm button 664 and a cancel button 666, whereby the user may select to confirm the display of user guidance in the guidance display 614 via the confirm button 664, or select not to display user guidance in the guidance display 614 via the cancel button 666. In other embodiments, different display and/or control elements may be used to prompt the user to request, enable, disable confirm, or cancel the display of user guidance, such as checkboxes, radio buttons, etc. In still further embodiments, the user may not be prompted to request, enable, disable, confirm, or cancel the display of user guidance, and user guidance may be automatically displayed, for example, if a proficiency score of the user is below a threshold proficiency value, as described above in relation to FIG. 3B.

In this way, various examples are provided for enabling optimally leveraging the real estate on the display screen of the device such as a smartphone or a tablet efficiently, from time to time during the workflow, without causing any inconvenience to the user.

Referring now to FIG. 7A, a user proficiency plot 700 is shown illustrating an improvement in a proficiency of a user of an ultrasound device as a function of practicing duration. User proficiency plot 700 includes an example learning curve 702 and an example learning curve 704. In an embodiment, learning curves 702 and 704 show the proficiency of a user on a first pre-set and a second pre-set, respectively, where the first pre-set and the second pre-set may correspond to anatomical features for which ultrasound images are being acquired. For example, pre-set 1 may correspond to a liver pre-set, and pre-set 2 may correspond to a spleen pre-set. In other embodiments, other or additional learning curves 702 and 704 corresponding to other pre-sets (e.g., other target anatomical features) may be depicted on plot 700. Thus, the totality of learning curves depicted on plot 700 may collectively describe an ultrasound operator's proficiency across a plurality of pre-sets covering a variety of different anatomical regions and target features, spanning a time period corresponding to the user's experience, whereby the plot 700 may provide a comprehensive representation of the user's proficiency (e.g., a snapshot).

Learning curves 702 and 704 are plotted on coordinate axes where a vertical axis 720 corresponds to the user's proficiency score, and a horizontal axis 722 corresponds to a practicing duration in time. The learning curves 702 and 704 of user proficiency plot 700 show the user's growth in proficiency as a function of time spent practicing, whereby as practice increases, proficiency grows slowly during a first duration (e.g., when the user is a novice), increases more rapidly during a second duration (e.g., as the user gains experience), and decreases after a threshold proficiency value is achieved (e.g., indicated in FIG. 7A by proficiency threshold line 710), until a point at which no further growth in proficiency is achieved. For example, learning curve 702 may depict the user's growing proficiency on a liver pre-set, characterized by an early slow-growth stage, a subsequent faster-growth stage, and a final slow-growth stage after which the user has obtained a high level of proficiency in ultrasound examinations of a patient's liver. Similarly, learning curve 704 may depict the user's growing proficiency on a spleen pre-set, characterized by a similar early slow-growth stage, a subsequent faster-growth stage, and a final slow-growth stage after which the user has obtained a high level of proficiency in ultrasound examinations of a patient's spleen. It should be appreciated that the duration of the slow growth and faster growth stages may be different for different pre-sets, such that the learning curves 702 and 704 may not have the same shape or be described by the same function.

As described above, the proficiency threshold line 710 may indicate a score at which the user may be determined to be proficient. For example, the proficiency threshold line 710 may correspond to a user proficiency score of 100, where a user score above 100 indicates proficiency, and a user score below 100 indicates a lack of proficiency. The proficiency threshold line 710 may divide the area of the plot into a proficiency stage portion 706 and an early stage portion 708. For example, a user score point 712 on the learning curve 702 may represent a user score of 110, which is above the proficiency threshold line 710 (e.g., representing 100 points), indicating that the user falls within the proficiency stage portion 706 (e.g., indicating that a user is proficient on a pre-set associated with learning curve 702). On the other hand, a user score point 714 on the learning curve 702 may represent a user score of 15, which is below the proficiency threshold line 710, indicating that the user falls within the early stage portion 706 (e.g., indicating that the user is not proficient on the pre-set associated with learning curve 702).

In some examples, the proficiency threshold 710 may be a common threshold that may be applied across all pre-sets. For example, the same proficiency threshold 710 may be utilized to determine whether or not a user is proficient for the first pre-set having learning curve 702 and the second pre-set having corresponding learning curve 704. Similarly, for additional different pre-sets, that have the same learning curve or different learning curves, the same proficiency threshold may be applied.

However, in some examples, as shown in FIG. 7B, each pre-set may have its own proficiency threshold. For example, proficiency threshold 710 may be utilized to determine if the user is proficient with respect to imaging for the first pre-set having learning curve 702, and a second different proficiency threshold 709 may be utilized to determine if the user is proficient for the second pre-set having learning curve 704. Similarly, different threshold proficiencies may be applied for additional different pre-sets having different learning curves. Further, in some examples, the threshold may be based on a practice duration required to achieve a steady plateau (that is, final slow-growth phase) in the learning curve, the steady plateau phase after an exponential growth phase (that is, intermediate fast-growth phase). In other words, the threshold for a given pre-set may be based on a corresponding learning curve for the pre-set. As a non-limiting example, the proficiency threshold may be lower for pre-sets that have a smaller duration to reach the final slow-growth phase, and the proficiency threshold may be greater for pre-sets that require a longer duration to reach the final slow-growth phase. Further, when two or more pre-sets have the same learning curve, their corresponding proficiency thresholds may be the same.

The horizontal distance between learning curves 702 and 704 may indicate an order and an amount of time between gaining proficiency in a first pre-set and gaining proficiency in a second pre-set. For example, learning curve 702 starts at an earlier time than learning curve 704 (e.g., learning curve 702 is further to the left on the horizontal axis 722 than learning curve 704), which may indicate that the user began gaining proficiency on the first pre-set prior to gaining proficiency on the second pre-set; that the user began to gain proficiency on the second pre-set at a time when the user's proficiency on the first pre-set was growing steadily; that the user achieved a high level of proficiency on the first pre-set prior to achieving a high level of proficiency on the second pre-set; and that the user ultimately achieved the same level of proficiency on both pre-sets (e.g., above the proficiency threshold line 710).

Further, a degree of similarity between the learning curves displayed in plot 700 may correspond to a degree to which the skills developed in a first pre-set transfer to a second pre-set. For example, the similarity of learning curves 702 and 704 in plot 700 may indicate that the proficiency gained in the first pre-set did not significantly transfer to the second pre-set, since the user was not able to achieve a high level of proficiency on the second pre-set in a shorter duration than it took to achieve a high level of proficiency on the first pre-set (e.g., the learning curves 702 and 704 both extend for an equal horizontal length). Similarly, the user did not achieve steady growth in proficiency on the second pre-set faster (e.g., within a shorter duration) than it took the user to achieve steady growth in proficiency on the first pre-set (e.g., the initial stage of the learning curve 702 has the same shape as the initial stage of the learning curve 704).

Thus, the user proficiency plot 700 provides a way to represent the development of an ultrasound operator's proficiency across a plurality of diagnostic ultrasound procedures, over the time that the operator spent practicing. This graphical representation may be used to determine what, when, and how long automated user guidance may be provided to operators of varying levels of proficiency, by determining a set of functions that describe growth in proficiency in acquiring ultrasound images over time, and determining how a proficiency growth function that describes proficiency improvement on one pre-set relates to other proficiency growth functions that describe proficiency improvement on other pre-sets.

For example, an ultrasound operator's proficiency growth function for a liver pre-set may be estimated and/or extrapolated based on a comparison of the operator's historical proficiency scores with the historical proficiency scores of a plurality of operators in performing ultrasound examinations of livers of patients. The operator's proficiency growth function for the liver pre-set may allow a processor of an ultrasound system (e.g., the ultrasound system 100 of FIG. 1) to extrapolate and estimate feature proficiency scores of the operator as a function of practice time, in order to notify the operator how many estimated hours they might practice to achieve a level of proficiency. The processor may select which forms of user guidance to display to the operator based on where the operator's current proficiency score is positioned on the operator's extrapolated learning curve. If an operator's proficiency score indicates that the operator is likely to be in an early slow growth stage, the processor may display user guidance designed to accelerate the acquisition of basic skills. If an operator's proficiency score indicates that the operator is moving beyond an early slow growth stage, the processor may stop displaying user guidance designed to accelerate the acquisition of basic skills, and may display other forms of user guidance designed to improve reproducibility (e.g., an intermediate skill). Thus, a selection and display of guidance based on a user's position along an estimated learning curve for the user may lead to a more precise customization of guidance than a selection and display of guidance based on a user's proficiency score alone.

The plot 700 may be used in the development of AI algorithms to determine when and what guidance to display to ultrasound operators. For example, historical data collected over a plurality of ultrasound operators for a given pre-set may allow for the determination of a generalized learning curve for that pre-set. The historical data may be used to train a machine learning algorithm (e.g., a neural network, etc.) to determine when a specific type of guidance may be displayed in order to maximize a growth in proficiency. For example, a neural network trained on historical data may determine that displaying reference ultrasound images is most effective not when a user achieves a certain proficiency score, but rather when a user is approaching an inflection point of the user's learning curve, and may further determine the precise point at which it is most helpful to the user to display a reference ultrasound image. Alternatively, a neural network trained on historical data may determine that displaying textbook anatomical images as user guidance is effective at the beginning of an initial slow-growth stage, but is not effective at the end of the initial slow-growth stage, in a way that may not be determined by a user's proficiency score alone (e.g., because the initial slow growth stage may last longer for some users than for others). Likewise, the neural network may determine the precise point at which it is most helpful to display textbook anatomical images to new users.

The historical data may also be used to generate general guidelines for displaying user guidance that is applicable to all users. For example, it may be determined from historical data collected from a plurality of users that learning curves for one pre-set tend to be shorter than learning curves for a different pre-set (e.g., that users tend to develop proficiency in acquiring images of a uterus faster than acquiring images of a lung, or that users tend to develop proficiency in acquiring images of a spleen faster than acquiring images of a liver, and so forth). As a result, it may be determined that users may gain proficiency across a plurality of pre-sets faster if the users first gain proficiency in pre-sets associated with shorter learning curves. Further, from a comparison of the historical data of a user with the historical data from a plurality of users, it may be determined that the user may obtain a benefit in terms of growth in proficiency by practicing on a plurality of pre-sets in a specified order, for example, where pre-sets with shorter estimated learning curves are practiced before pre-sets with longer estimated learning curves.

Thus, the proficiency assessments carried out as disclosed herein, based on proficiency scores assigned in accordance with rubrics established for different pre-sets corresponding to specific anatomical regions and target anatomical features, which are stored and used to generate user-specific learning curves for the different pre-sets, provide a robust framework for dynamically scoring user performance on ultrasound examinations. The resulting scores may be used in turn as the basis for automatically generating customized user guidance dynamically, where the selection and timing of the user guidance may be adjusted over time to maximize the impact of the user guidance on increased operator proficiency.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for medical imaging, comprising:
receiving, at a processing unit of an ultrasound system, information generated by an ultrasound probe, scan settings, and historical information, wherein the historical information is stored in a proficiency database electronically coupled to the processing unit; determining, using the processing unit, a proficiency score of a user, the proficiency score corresponding to a proficiency of the user in imaging with the ultrasound system, wherein the proficiency score is based on the historical information stored in the proficiency database relating to the user's operation of the ultrasound system and a real-time ultrasound image being acquired by the ultrasound probe, and wherein the ultrasound system is a handheld ultrasound imaging system, and wherein the proficiency score is further determined based on contact pressure at a tip of the ultrasound probe;

based on the proficiency score, automatically adjusting an amount of a guidance provided to the user on a graphical user interface of a display device coupled to the ultrasound system; and automatically displaying an indication of the proficiency received from the proficiency database, the real-time ultrasound image acquired by the ultrasound probe coupled to the display device, and the guidance on the graphical user interface, wherein the guidance is a partially transparent image overlay over a portion of the real-time ultrasound image, and wherein the guidance includes real-time guidance including a reference anatomical image based on the displayed real-time ultrasound image and the proficiency, and an indication of a direction and/or amount of pressure to apply to the tip of the ultrasound probe.

2. The method of claim 1, wherein adjusting the amount of the guidance includes responsive to the proficiency score less than a threshold score for an anatomical region, automatically turning ON the guidance for the user during a current imaging session, and responsive to the proficiency score greater than the threshold score for the anatomical region, automatically turning OFF the guidance for the user during the current imaging session.

3. The method of claim 2, wherein the guidance further includes a contextual user guidance.

4. The method of claim 3, further comprising, during the current imaging session, providing, on the display device, one or more indications that are not based on the proficiency score.

5. The method of claim 3, wherein the display device is a rectangular display of a smartphone or a tablet and guidance is displayed on a portion of the display device along with a real-time or near real-time ultrasound image acquired during the current imaging session, and wherein the guidance is displayed over a top, narrow portion of the real-time or near real-time ultrasound image.

6. The method of claim 1, further comprising:
monitoring a speed of the user in acquiring a desired image during a current imaging session; and
responsive to the speed of the user less than a threshold speed of acquisition, automatically turning ON the guidance.

7. The method of claim 6, further comprising:
prior to automatically turning ON the guidance responsive to the speed of the user greater than the threshold speed, displaying, on the display device, an indication of a duration remaining before the guidance is turned ON, and/or prior to automatically turning ON the guidance responsive to the speed of the user less than the threshold speed, displaying, on the display device, a user guidance prompt for activating the guidance, the user guidance prompt including a confirmation button for turning ON the guidance and a cancellation button for not turning ON the guidance.

8. The method of claim 1, wherein the proficiency score is determined based on progressively tracking one or more proficiency parameters, the one or more proficiency parameters including, for a given view acquired by the user, an image quality of the given view, a time taken to acquire the given view, an accuracy of scan plane in the given view, a number of practice hours for the user, a number of imaging examinations performed by the user, reproducibility of the given view, and repeatability of acquiring the given view consistent with the proficiency of the user.

9. The method of claim 8, further comprising, evaluating a current session score based on the one or more proficiency parameters, wherein evaluating the current session score includes comparing a first standard deviation between a relative positioning of anatomical features in the real-time ultrasound image with a second standard deviation between the relative positioning of the anatomical features in ultrasound images previously acquired by the user, and updating the proficiency score based on the current session score.

10. The method of claim 1, wherein the proficiency score is determined based on an evaluation rubric for each of a plurality of proficiency levels, the evaluation rubric indicating a qualitative and/or a quantitative requirement pertaining to one or more proficiency parameters including an image quality of a view acquired by the user, a time taken to acquire the view, an accuracy of scan plane in the view, a number of practice hours for the user, a number of imaging examinations performed by the user, reproducibility of the view, and repeatability of acquiring the view consistent with the proficiency of the user.

11. The method of claim 1, wherein the historical information includes a number of practice hours completed, a number of ultrasound exams completed, and/or an assessment of a reproducibility and/or repeatability of an ultrasound procedure by the user.

12. The method of claim 1, wherein the reference anatomical image is of a target scan plane or an illustration with annotated information.

13. The method of claim 1, wherein the historical information is used to train a machine learning algorithm to determine when a type of guidance is displayed to maximize growth in proficiency.

14. A method, comprising:
progressively tracking a proficiency score for imaging with a handheld ultrasound system including an ultrasound probe via a processor of the handheld ultrasound system, the proficiency score tracked for a user with respect to each of a plurality of anatomical regions and stored on a proficiency database electrically coupled to the processor of the handheld ultrasound system and the proficiency score determined based on contact pressure at a tip of the ultrasound probe;
during a current imaging session,
determining a current proficiency score for a current anatomical region, and responsive to the current proficiency score less than a threshold score for the current anatomical region, automatically displaying a guidance on a portion of a display coupled to the handheld ultrasound system along with an acquired medical image, wherein the guidance includes an indication of a direction and amount of pressure to apply to the tip of the ultrasound probe;
otherwise, displaying, on a rectangular smartphone or tablet display coupled to the handheld ultrasound system, the acquired medical image without the guidance; and
when the guidance is not displayed, additionally monitoring one or more selected proficiency parameters during the current imaging session, and
responsive to at least one selected proficiency parameter not meeting a corresponding threshold requirement, automatically displaying the guidance, and prior to automatically displaying the guidance, displaying, on the rectangular smartphone or tablet display, an indication of a duration remaining before the guidance is displayed, and/or further comprising, prior to automatically displaying the guidance, displaying, on the display, a user guidance prompt for displaying the guidance, the user guidance prompt including a confirmation button for displaying the guidance and a cancellation button for not displaying the guidance, wherein the indication and the user guidance prompt are displayed as a transparent overlay on a top, narrow portion of the acquired medical image on the display.

15. The method of claim 14, further comprising, during the current imaging session, displaying, on the display, an indication of a proficiency stage of the user, the proficiency stage with respect to the current anatomical region and based on the proficiency score; and wherein the guidance includes one or more of a real-time guidance and contextual guidance.

16. The method of claim 14, wherein the current proficiency score is determined based on progressively tracking one or more proficiency parameters, the one or more proficiency parameters including an image quality of a view of the current anatomical region, a time taken to acquire the view, an accuracy of scan plane in the view, a number of practice hours for the user corresponding to the current anatomical region, a number of imaging examinations performed by the user corresponding to the current anatomical region of interest, reproducibility of the view, and repeatability of acquiring the view consistent with the current proficiency score of the user.

17. A system, comprising:
an ultrasound probe;
a display device coupled to the ultrasound probe; and
a processor communicably coupled to the display device, a non-transitory memory storing proficiency data for a plurality of users, the proficiency data including a proficiency score for each of a plurality of anatomical regions of interest for each of the plurality of users and based a determined contact pressure at a tip of the ultrasound probe, and including instructions that when executed cause the processor to:
for each of the plurality of users, progressively monitor and update the proficiency score for each of the plurality of anatomical regions of interest; and
during an imaging session performed by a user for a current anatomical region,
acquire an ultrasound image via the ultrasound probe;
display, on an active portion of the display device, the acquired ultrasound image;
display, on a guidance portion of the display device, real-time and contextual guidance relative to a reference anatomical image, wherein the contextual guidance includes a direction and/or amount of pressure to apply to the tip of the ultrasound probe;
determine a proficiency stage for the user based on the stored proficiency data for the plurality of users for the current anatomical region based on a corresponding proficiency score of the user for the current anatomical region;
adjust a level of real-time and a level of contextual guidance based on the proficiency stage for the current anatomical region, wherein the real-time guidance is based on the acquired ultrasound image, and display the real-time and contextual guidance as an image overlay over a portion of the reference anatomical image, including displaying a representation of the ultrasound probe; and
display, on a second portion of the active portion, an indication of the proficiency stage of the user.

18. The system of claim 17, wherein the proficiency score is based on a predefined rubric for measuring a proficiency level, the predefined rubric based on qualitative and/or quantitative criteria pertaining to one or more proficiency parameters, the one or more proficiency parameters including, for a given view acquired by a given user, an image quality of the given view, a time taken to acquire the given view, an accuracy of scan plane in the given view, a number of practice hours, a number of imaging examinations, reproducibility of the given view, and repeatability of acquiring the given view consistent with the proficiency score of the given user.

19. The system of claim 18, wherein the level of real-time and/or contextual guidance is adjusted by increasing the level of real-time and/or contextual guidance provided to the user when the corresponding proficiency score is less than a threshold score, and decreasing the level of real-time and/or contextual guidance provided to the user when the corresponding proficiency score is greater than the threshold score, the threshold score based on the current anatomical region.

20. The system of claim 17, wherein the non-transitory memory storing proficiency data for the plurality of users is a proficiency database electronically coupled to the processor, and wherein the instructions further include to generate user-specific learning curves and to determine a type of the real-time and/or contextual guidance to display based on the user-specific learning curves.

21. The system of claim 17, wherein the reference anatomical image includes a representation of a target anatomical feature in the acquired ultrasound image, wherein the reference anatomical image includes component anatomical structures identified via labels, and wherein the instructions further cause the processor to display the reference anatomical image displayed while displaying, on the active portion of the display device, the acquired ultrasound image adjacent to the reference anatomical image.

22. The system of claim 17, wherein the real-time guidance is superimposed on the contextual guidance.

* * * * *